United States Patent [19]

Crooij et al.

[11] 3,994,887

[45] Nov. 30, 1976

[54] 7-(3-SUBSTITUTED UREIDO) CEPHALOSPORINS

[75] Inventors: Pierre Crooij, Genval; Alain Colinet, La Hulpe, both of Belgium

[73] Assignee: Recherche et Industrie Therapeutiques (R.I.T.), Belgium

[22] Filed: June 4, 1975

[21] Appl. No.: 583,362

Related U.S. Application Data

[60] Division of Ser. No. 361,393, May 17, 1973, Pat. No. 3,912,728, which is a continuation-in-part of Ser. No. 265,371, June 22, 1972, abandoned.

[52] U.S. Cl. .............................. 260/243 C; 424/246
[51] Int. Cl.² ...................................... C07D 501/36
[58] Field of Search ................................ 260/243 C

[56] References Cited

UNITED STATES PATENTS 3,833,568  9/1974  Dolfini et al. .................... 260/243 C Primary Examiner—Nicholas S. Rizzo
Assistant Examiner—David E. Wheeler
Attorney, Agent, or Firm—Alan D. Lourie; William H. Edgerton

[57] ABSTRACT

Cephalosporin compounds with 3-substituted ureido or -thioureido group at position 7 and hydrogen or heterocyclicthiomethyl groups at position 3 are prepared. These compounds are antibacterial agents.

4 Claims, No Drawings

7-(3-SUBSTITUTED UREIDO) CEPHALOSPORINS

This is a division of application Ser. No. 361,393 filed May 17, 1973 now U.S. Pat. No. 3,912,728 filed Oct. 14, 1975, which application was a continuation-in-part of application Ser. No. 265,371, filed June 22, 1972, now abandoned.

This invention relates to new chemical compounds known as cephalosporins, which compounds possess antibacterial activity.

The compounds of this invention are represented by the following structural formula I:

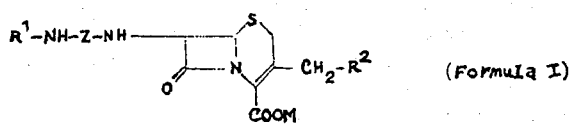

(Formula I)

wherein
R$^1$ is either saturated or unsaturated aliphatic group of up to 6 carbon atoms with straight or branched chain, unsubstituted or substituted with from one to two groups selected from the group consisting of halogen, hydroxy, methoxy, azido, amino, carboxy, cyano, nitro, diloweralkylamino (each alkyl containing from one to four carbon atoms), aryl, saturated or unsaturated cycloalkyl of up to 6 carbon atoms and 5 or 6 membered heterocyclic ring containing one to four atoms of N, O or S, said aryl, cycloalkyl and heterocyclic ring being unsubstituted or substituted with one or two groups selected from the group consisting of halogen, hydroxy, cyano, nitro, acetamido, sulfamoyl, mercapto, methylthio, lower alkyl, lower alkoxy and diloweralkylamino (each alkyl or alkoxy containing from one to four carbon atoms); aryl, saturated or unsaturated cycloalkyl of up to 6 carbon atoms or 5 or 6 membered heterocyclic ring containing one to four atoms of N, O or S, said aryl, cycloalkyl or heterocyclic ring being unsubstituted or substituted with one or two groups selected from the group consisting of halogen, hydroxy, cyano, nitro, acetamido, sulfamoyl, mercapto, methylthio, lower alkyl, lower alkoxy and diloweralkylamino (each alkyl or alkoxy containing from one to four carbon atoms);

Z is O or S;

R$^2$ is hydrogen, pyridinium, N-piperidino- or N-piperazino- dithiocarboxylate or S-Het wherein Het is a 5 or 6 membered heterocyclic ring containing one or more atoms of N, O or S, with or without ring substituents such as halogen, lower alkyl, lower alkoxy, amino, lower akylamino or dialkylamino, each alkyl or alkoxy containing from 1 to 4 carbon atoms; and M is hydrogen, alkali metal cation, alkaline earth cation, or a non toxic organic ammonium cation.

Examples of 5 or 6 membered heterocyclic rings containing one or more atoms of N, O or S, with or without ring substituents as indicated hereinabove are

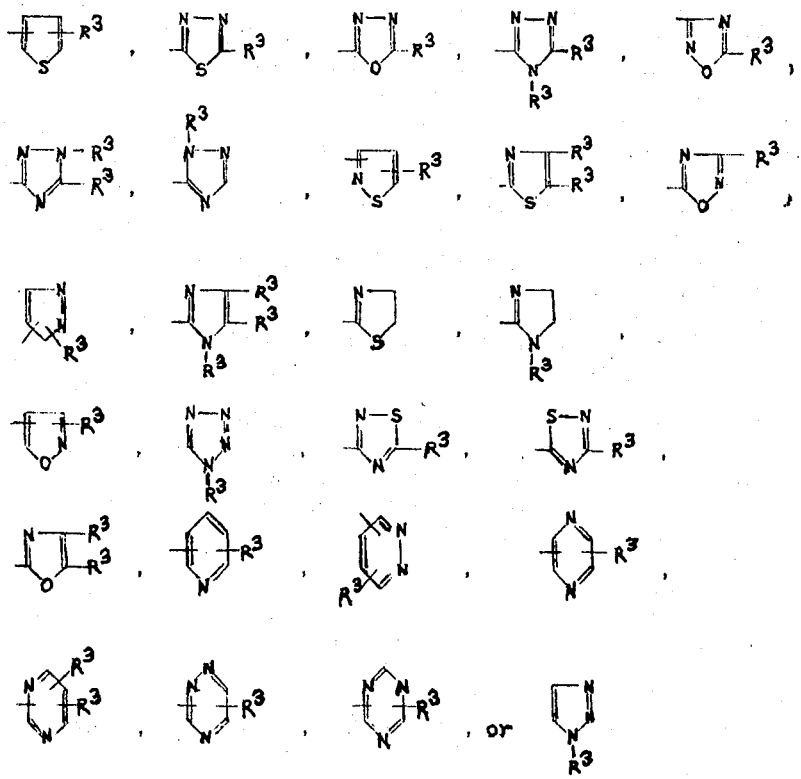

wherein
R$^3$ is hydrogen, halogen, lower alkyl, lower alkoxy, nitro, acetamido, sulfamoyl, amino, lower alkylamino or dialkylamino, each alkyl or alkoxy containing from 1 to 4 carbon atoms.

The preferred compounds are those wherein R$^1$ is unsubstituted or substituted aliphatic group of up to 6 carbon atoms and wherein R$^2$ is S-Het wherein Het is 1,3,4-thiadiazol-2-yl, 1,3,4-triazol-2-yl, 1,2,3-triazol-5-yl, 1,2,4-triazol-3-yl, 1,2,4-oxadiazol-3(5)-yl, 1,3,4-oxadiazol-2-yl, 1,2,4-thiadiazol-3(5)-yl, tetrazol-5-yl, pyridyl, pyrimidyl, pyrazinyl or 2-thiazolin-2-yl, all of which may be unsubstituted or substituted with one or more of the substituents which were enumerated above. Particularly preferred are the lower alkyl (1-4 carbon atoms) substituted 5-membered heterocyclic compounds, that is, 5-alkyl-1,3,4-thiadiazol-2-yl, 5(3)-alkyl-1,2,4-oxadiazol-3(5)-yl, 5-alkyl-1,3,4-oxadiazol-2-yl, 1-alkyl-1,2,3-triazol-5-yl, 1-alkyl-1,2,4-triazol-3-yl, 5-alkyl-1,2,4-triazol-3-yl, 5-alkyl-1,3,4-triazol-2-yl, 1,5-dialkyl-1,2,4-triazol-3-yl and 1-alkyl-tetrazol-5-yl.

The compounds of this invention are prepared by a series of reactions, the essential reactions being first
1. either catalytic hydrogenation of the 3-acetoxy group to yield the 3-methyl group or displacement of the 3-acetoxy group of 7-aminocephalosporanic acid (7-ACA) with the desired mercaptoheterocyclic compound to give the 3-heterocyclicthiomethyl-substituted compound and then reaction of the 7-amino group of 7-ACA with the appropriate isocyanate or isothiocyanate or
2. reaction of 7-ACA with phosgene (or thiophosgene) to yield isocyanato (or isothiocyanato) cephalosporanic acid which is reacted with the appropriate amine of formula $R^1NH_2$ and then either catalytic hydrogenation of the 3-acetoxy group to yield the 3-methyl group or displacement of the 3-acetoxy group of 7-ACA with the desired mercaptoheterocyclic compound.

Alternatively, the products of formula 1 are also obtained by reaction between the substituted carbamoyl or thiocarbamoyl halide, preferably chloride, and the 3-substituted-7-amino-3-cephem-4-carboxylic acid in a non reactive solvent, the starting carbamoyl or thiocarbamoyl halide being prepared from phosgen or thiophosgen and the adequately substituted amine in a non reactive solvent.

The catalytic hydrogenation is carried out in aqueous solution, preferably with a palladium catalyst on an inert carrier such as carbon or baryum sulfate, the starting 7-aminocephalosporanic acid being reacted in the form of a soluble salt, preferably an alkali metal salt as sodium salt.

The displacement reaction is carried out at neutral pH in a non reactive polar solvent such as water tetrahydrofuran, acetone or a water-acetone solvent system at a temperature comprised between 40° and 80° C until the reaction is completed as indicated by the disappearance of the acetoxy carbonyl band in the infrared absorption spectrum.

The treatment with the isocyanate is carried out in a tertiary amine — for instance, pyridine — or in a mixture of a tertiary amine with a non reactive organic solvent — for example, triethylamine and methylene chloride — at a temperature inferior to 80° C.

The order of the displacement reaction and the isocyanate treatment may be reversed.

When $R^1$ is substituted by hydroxy, mercapto, amino or carboxy, the corresponding reactant must obviously be adequately protected according to any method known from the art for such protection.

According to another embodiment of the present invention, the compounds of formula 1 wherein $R^1$ is amino-substituted are also obtained by selective catalytic hydrogenation of the corresponding azido substituted cephalosporin.

As indicated above, also included within the scope of the invention are the nontoxic alkali metal, alkaline earth or organic ammonium salts of formula I, all of which have antibacterial activity. These may be isolated directly from the final reaction or can be prepared from the free acid by reaction with the appropriate base.

The starting material for preparing the products of this invention are either known or readily preparable by known methods or described therein.

The products of this invention are antibacterial agents active against Gram-negative and Gram-positive organisms such as *Staph. aureus* including macrolides resistant *Staph. aureus* strains, *Aerobacter aerogenes*, *Klebsiella pneumoniae*, *Salmonella paratyphi*, *Shigella sonnei*, *Proteus mirabilis*, *Proteus morganii* and *Candida albicans* and particularly active against *Staph. aureus*, *E. coli* and *Klebsiella pneumoniae*.

For the preferred compounds of this invention as indicated above, the minimum inhibitory concentrations in the conventional agar-inclusion test are less than 2 microgram/ml. for certain Staphylococcus and less than 10 microgram/ml. for certain *E. coli* and *Klebsiella pneumoniae* strains.

The products of this invention may be administered by parenteral or oral route, being therefore formulated into adequate compositions in the same manner as other cephalosporin antibacterials. The dose that is administered to the subject will depend on the severity and type of infection as well as the general condition of the subject.

Among the preferred compounds of the invention are:

Group I compounds:
7-(3-n-propylureido)-3-(1,3,4-oxadiazol-2-ylthiomethyl)-3-cephem-4-carboxylic acid (compound RIT N° 3024)
7-(3-n-propylureido)-3-(5-methyl-1,3,4-oxadiazol-2-ylthiomethyl)-3-cephem-4-carboxylic acid (compound RIT N° 3008)

Group II compounds:
7-[3-(2-chloro-ethylureido)]-3-(5-methyl-1,3,4-thiadiazol-2-ylthiomethyl)-3-cephem-4-carboxylic acid (compound RIT N° 2892)
7-[3-(2-chloro-ethylureido)]-3-(5-methyl-1,3,4-oxadiazol-2-ylthiomethyl)-3-cephem-4-carboxylic acid (compound RIT N° 3007)
7-[3-(2-chloro-ethylureido)]-3-(1,3,4-triazol-2-ylthiomethyl)-3-cephem-4-carboxylic acid (compound RIT N° 3211)
7-[3-(2-chloro-ethylureido)]-3-(pyrimidin-2-ylthiomethyl)-3-cephem-4-carboxylic acid (compound RIT N° 3055)
7-[3-(2-chloro-ethylureido)]-3-(1-methyl-1H-tetrazol-5-ylthiomethyl)-3-cephem-4-carboxylic acid (compound RIT N° 3219)

Group III compounds:
7-(3-allylureido)-3-(5-methyl-1,3,4-thiadiazol-2-ylthiomethyl)-3-cephem-4-carboxylic acid (compound RIT N° 2746)
7-(3-allylureido)-3-(5-methyl-1,3,4-oxadiazol-2-ylthiomethyl)-3-cephem-4-carboxylic acid (compound RIT N° 3011)
7-(3-allylureido)-3-(5-methyl-1,3,4-triazol-2-ylthiomethyl)-3-cephem-4-carboxylic acid (compound RIT N° 3013)
7-(3-allylureido)-3-(2-thiazolin-2-ylthiomethyl)-3-cephem-4-carboxylic acid (compound RIT N° 2747)
7-(3-allylureido)-3-(1-methyl-1H-tetrazol-5-ylthiomethyl)-3-cephem-4-carboxylic acid (compound RIT N° 3241)

Group IV compounds:

7-(3-benzylureido)-3-(5-methyl-1,3,4-thiadiazol-2-ylthiomethyl)-3-cephem-4-carboxylic acid (compound RIT N° 2912)

7-(3-benzylureido)-3-(1,3,4-triazol-2-ylthiomethyl)-3-cephem-4-carboxylic acid (compound RIT N° 3212)

7-(3-benzylureido)-3-(pyrimidin-2-ylthiomethyl)-3-cephem-4-carboxylic acid (compound RIT N° 3056)

7-(3-benzylureido)-3-(1-methyl-1H-tetrazol-5-ylthiomethyl)-3-cephem-4-carboxylic acid (compound RIT N° 3220)

Group V compounds:
7-(3-p-chlorobenzylureido)-3-(5-methyl-1,3,4-thiadiazol-2-ylthiomethyl)-3-cephem-4-carboxylic acid (compound RIT N° 3210)

Group VI compounds:
7-(3-α-methylbenzylureido)-3-(5-methyl-1,3,4-thiadiazol-2-ylthiomethyl)-3-cephem-4-carboxylic acid (compound RIT N° 3203)

7-(3-α-methylbenzylureido)-3-(1,3,4-oxadiazol-2-ylthiomethyl)-3-cephem-4-carboxylic acid (compound RIT N° 3213)

7-(3-α-methylbenzylureido)-3-(5-methyl-1,3,4-oxadiazol-2-ylthiomethyl)-3-cephem-4-carboxylic acid (compound RIT N° 3217)

7-(3-α-methylbenzylureido)-3-(1-methyl-1H-tetrazol-5-ylthiomethyl)-3-cephem-4-carboxylic acid (compound RIT N° 3242)

As resulting from the following Tables I to VI, the above compounds of the invention are advantageous over the corresponding 3-acetoxymethyl compounds, i.e.:

7-(3-n-propylureido)cephalosporanic acid (compound RIT N° 3266) corresponding to the above Group I compounds 7-[3-(2-chloro-ethylureido)]cephalosporanic acid (compound RIT N° 3267) corresponding to the above Group II compounds 7-(3-allylureido)cephalosporanic acid (compound RIT N° 2758) corresponding to the above Group III compounds 7-(3-benzylureido)cephalosporanic acid (compound RIT N° 3265) corresponding to the above Group IV compounds 7-(3-p-chlorobenzylureido)cephalosporanic acid (compound RIT N° 3209) corresponding to the above Group V compounds 7-(3-α-methylbenzylureido)cephalosporanic acid (compound RIT N° 3208) corresponding to the above Group VI compounds The following Tables I to VI summarize the results of an in vivo mouse protection study in which a test compound is administered in graded dilutions to mice either subcutaneously in water or orally in a suitable suspending agent one hour after intravenous infection with uniformly lethal doses of S. aureus. The animals are observed for 3 days. The total dose required to protect 50% of the infected mice is designated as the $ED_{50}$, the most potent compounds having the lowest $ED_{50}$'s (the indicated results give the evolution of the $ED_{50}$ with time):

TABLE I

| | $ED_{50}$ of the Group I compounds | | | | | | | | | | | | |
|---|---|---|---|---|---|---|---|---|---|---|---|---|---|
| | Hours after subcutaneous administration | | | | | | | Hours after oral administration | | | | | |
| Compounds | 18 | 22 | 26 | 42 | 46 | 50 | 66 | 18 | 22 | 26 | 42 | 46 | 50 | 66 |
| 3024 | | | | 16 | >30 | >20 | >20 | | | | 43 | 48 | 57 | 80 |
| 3008 | | 12 | | 17 | >20 | >20 | >20 | | | 46 | 74 | >80 | >80 | >80 |
| 3266 | | | 7 | >20 | >20 | >20 | >20 | | | 57 | >80 | >80 | >80 | >80 |

TABLE II

| | $ED_{50}$ of the Group II compounds | | | | | | | | | | | | |
|---|---|---|---|---|---|---|---|---|---|---|---|---|---|
| | Hours after subcutaneous administration | | | | | | | Hours after oral administration | | | | | |
| Compounds | 18 | 22 | 26 | 42 | 46 | 50 | 66 | 18 | 22 | 26 | 42 | 46 | 50 | 66 |
| 2892 | | | | 14 | 10 | 17 | >20 | | 25 | >80 | >80 | >80 | >80 | >80 |
| 3007 | | | 8 | 8 | 10 | 11 | >20 | | | 44 | 74 | >80 | >80 | >80 |
| 3211 | | | | 15 | >20 | >20 | >20 | | | | 55 | 64 | >80 | >80 |
| 3055 | 12 | >20 | >20 | >20 | >20 | >20 | >20 | | | | | | | |
| 3219 | | 14 | >20 | >20 | >20 | >20 | >20 | | 40 | 75 | >80 | >80 | >80 | >80 |
| 3267 | >20 | >20 | >20 | >20 | >20 | >20 | >20 | 65 | 78 | >80 | >80 | >80 | >80 | >80 |

TABLE III

| | $ED_{50}$ of the Group III compounds | | | | | | | | | | | | |
|---|---|---|---|---|---|---|---|---|---|---|---|---|---|
| | Hours after subcutaneous administration | | | | | | | Hours after oral administration | | | | | |
| Compounds | 18 | 22 | 26 | 42 | 46 | 50 | 66 | 18 | 22 | 26 | 42 | 46 | 50 | 66 |
| 2746 | | | | 14 | 17 | 20 | >20 | | | | >40 | >40 | >40 | >40 |
| 3011 | | | 12 | >20 | >20 | >20 | >20 | | | 35 | >80 | >80 | >80 | >80 |
| 3013 | | 11 | 16 | >20 | >20 | >20 | >20 | | | 46 | 61 | >80 | >80 | >80 |
| 2747 | | | | 7 | 11 | >20 | >20 | | | | 36 | 36 | 55 | >80 |
| 3241 | | | 11 | >20 | >20 | >20 | >20 | | | 39 | 73 | >80 | 80 | >80 |
| 2758 | | 14 | 19 | >20 | >20 | >20 | >20 | | 56 | 63 | >80 | >80 | >80 | >80 |

TABLE IV

ED$_{50}$ of the Group IV compounds

| Compounds | Hours after subcutaneous administration | | | | | | | Hours after oral administration | | | | | | |
|---|---|---|---|---|---|---|---|---|---|---|---|---|---|---|
| | 18 | 22 | 26 | 42 | 46 | 50 | 66 | 18 | 22 | 26 | 42 | 46 | 50 | 66 |
| 2912 | | | <5 | 8 | 8 | | 14 | | 27 | 40 | 51 | >80 | >80 | >80 |
| 3212 | | | | 8 | 10 | 12 | 19 | | | | 70 | 77 | >80 | >80 |
| 3056 | | | | 9 | 11 | 11 | 13 | | | 27 | 55 | 55 | 55 | >80 |
| 3220 | | | | 12 | 17 | >20 | >20 | | | | 55 | >80 | >80 | >80 |
| 3265 | | | 6 | >20 | >20 | >20 | >20 | | | 34 | >80 | >80 | >80 | >80 |

TABLE V

ED$_{50}$ of the Group V compounds

| Compounds | Hours after subcutaneous administration | | | | | | | Hours after oral administration | | | | | | |
|---|---|---|---|---|---|---|---|---|---|---|---|---|---|---|
| | 18 | 22 | 26 | 42 | 46 | 50 | 66 | 18 | 22 | 26 | 42 | 46 | 50 | 66 |
| 3210 | | | | | 7 | 11 | 12 | | | | | 47 | 64 | 67 |
| 3209 | | | | | 7 | 15 | 16 | | | | | 54 | 73 | 78 |

TABLE VI

ED$_{50}$ of the Group VI compounds

| CUZ,1/64 Compounds | Hours after subcutaneous administration | | | | | | | Hours after oral administration | | | | | | |
|---|---|---|---|---|---|---|---|---|---|---|---|---|---|---|
| | 18 | 22 | 26 | 42 | 46 | 50 | 66 | 18 | 22 | 26 | 42 | 46 | 50 | 66 |
| 3203 | | | | >20 | >20 | >20 | >20 | | | | 66 | >80 | >80 | >80 |
| 3213 | | | 14 | >20 | >20 | >20 | >20 | | | 59 | 72 | >77 | >80 | >80 |
| 3217 | | | 12 | 17 | >20 | >20 | >20 | | | >80 | >80 | >80 | >80 | >80 |
| 3242 | | 14 | 19 | >20 | >20 | >20 | >20 | | 50 | 63 | >80 | >80 | >80 | >80 |
| 3208 | >20 | >20 | >20 | >20 | >20 | >20 | >20 | 64 | >80 | >80 | >80 | >80 | >80 | >80 |

In the following examples which are presented to illustrate the invention further but are not to be construed to limit the scope thereof, the indicated R$_f$ have been determined by thin layer chromatography on SELECTA TLC Plastic Sheets F 1500 LS 254 Silica gel (a product of K. SCHLEICHER and SCHULL, W. Germany) and the nmr spectra have been recorded on a Perkin Elmer R-12 (60 Mc) using tetramethylsilane as internal reference (solvent: mixture of hexadeuterodimethylsulfoxide and deuteroxide), the chemical shift (δ) being expressed in p.p.m.

EXAMPLE 1

To a cooled suspension of 7-ACA (13.6 g) in distilled water (50 ml) are added by small fractions 89 ml of N NaHCO$_3$ in water and 50 ml of acetone. To the solution are added a mixture of 16 ml of 0.2 M NaH$_2$PO$_4$ in water and 84 ml. of 0.2 M Na$_2$HPO$_4$ in water (pH of the mixture: 7.4) and a mixture of 5-mercapto-2-methyl-1,3,4-thiadiazole (10.6 g, 80 mmol) in acetone (40 ml) and N NaHCO$_3$ in water (60 ml). The flask which contained the 5-mercapto-2-methyl-1,3,4-thiadiazole is rinsed out with a mixture of water (10 ml), acetone (10 ml) and N NaHCO$_3$ in water (10 ml) (pH of the mixture: 6.8) which is added to the reaction medium —which is then heated on an oil bath (70° C) to gentle reflux with stirring for 3¾ hours. After that reaction period, the pH of the medium is 7. The flask is placed in an ice bath and, when the temperature of the medium reaches 10° C, the solution is slowly acidified with 12 N HCl (17 ml) to pH 3.9, the temperature being then −2° C.

The precipitate is filtered, washed with 3 portions (10 ml) of water, 3 portions (100 ml) of acetone and 3 portions (50 ml) of ethyl ether.

The dried crude product (11.8 g) is suspended in water (140 ml) and concentrated aqueous ammonium hyroxide (3.44 ml) is added slowly with vigorous stirring to reach complete solution at pH 7.00 under pH stat control. Charcoal (10 g) and, 10 minutes later, Dicalite SH (10 g) (an infusorial earth filter aid sold by DICALITE EUROPE NORD, Brussels, Belgium) is then added thereto. After 15 minutes standing, the mixture is filtered and the adsorbent is washed with water (20 ml) and 1/1 water-acetone (40 ml). The solution (pH 6.7) is acidified over a one hour period with 12 N HCl to pH 3.9. Acetone (80 ml) is added to facilitate the filtration. The precipitate is filtered, washed with water, acetone and ether to yield 7-amino-3(2-methyl-1,3,4-thiadiazol-5-ylthiomethyl)-3-cephem-4-carboxylic acid (8.27 g).

EXAMPLE 2

To a 6.888 g. aliquot of 7-amino-3-(2-methyl-1,3,4-thiadiazol-5-ylthiomethyl)-3-cephem-4-carboxylic acid in a one liter reaction flask are added methylene chloride (500 ml), triethylamine (5.6 ml) and methylisocyanate (3.5 ml). The mixture is stirred at room temperature for 18 hrs. The solvent is then removed by evaporation under reduced pressure and the residue is taken up in acetic acid (20 ml) and ethyl acetate (250 ml).

After filtration, ethyl ether is added to precipitate 7-(3-methylureido)-3-(2-methyl-1,3,4-thiadiazol-5-ylthiomethyl)-3-cephem-4-carboxylic acid (5.168 g).

R$_f$ =0.10 (± 0.10) in the system methylisobutylketone/methanol/formic acid 60/6/2, detection with bromcresol green and KMnO$_4$; nmr : 2.58 s (3H), 2.66 s (3H), 3.37 d (1H)(J 14 c./sec.), 3.74 d (1H)(J 14 c./sec.), 4.18 d (1H)(J 18 c./sec.), 4.52 d (1H)(J 18 c./sec.), 5.00 d (1H)(J 4.7 c./sec.), 5.60 d (1H)(J 4.7 c./sec.).

EXAMPLE 3

7-ACA (13.65 g) and 2-thiazoline-2-thiol (11.92 g) are suspended in 500 ml. of phosphate buffer 0.2 M (Na$_2$HPO$_4$/NaH$_2$PO$_4$) pH 6.5. To the suspension are added with stirring 12.6 g. of NaHCO$_3$ and 250 ml. of acetone. The reaction medium is heated for 2¼ hrs with stirring on a 80° C water bath. The solution is then treated with charcoal, cooled (5°–10° C) and acidified to pH 4 with 2 N hydrochloric acid. The obtained suspension is diluted with acetone and stirred for 15–20 minutes. The precipitate is filtered, washed with water, acetone and ethyl ether and dried under reduced pressure to yield 7-amino-3-(2-thiazolin-2-ylthiomethyl)-3-cephem-4-carboxylic acid.

EXAMPLE 4

In a one liter reaction flask and to a 6.528 g. aliquot of 7-amino-3-(2-thiazolin-2-ylthiomethyl)-3-cephem-4-carboxylic acid prepared according to the procedure described in Example 3 are added methylene chloride (500 ml), tributylamine (9.5 ml) and methylisocyanate (3.5 ml). The mixture is stirred at room temperature for 15 hrs and then at 50° C for 6 hrs. The solvent is then removed by evaporation under reduced pressure and the residue is taken up in acetic acid (20 ml) and ethyl acetate (250 ml).

After filtration, ethyl ether is added to precipitate 7-(3-methylureido)-3-(2-thiazolin-2-ylthiomethyl)-3-cephem-4-carboxylic acid.

$R_f$ = 0.09 (± 0.10) in the system methylisobutylketone/methanol/formic acid 60/6/2, detection with bromcresol green and KMnO$_4$; nmr : 260 s (3H), 3.03 m (2H + 2H), 3.32 d (1H)(J 13 c./sec.), 3.67 d (1H)(J 13 c./sec.), 4.01 d (1H)(J 15 c.sec.), 4.39 d (1H) (J 15 c./sec.), 5.00 d (1H)(J 5 c./sec.), 5.60 d (1H) (J 5 c./sec.).

EXAMPLE 5

In a one liter reaction flask and to 5.360 g. of 7-amino-3-desacetoxy-cephalosporanic acid (7-ADCA) are added ethylisocyanate (2.16 ml) and pyridine (500 ml). The mixture is stirred at room temperature for 24 hrs. The unreacted 7-ADCA is separated by filtration. The solvent is removed by evaporation under reduced pressure, the residue is taken up in petroleum ether and 7-(3-ethylureido)-3-desacetoxy-cephalosporanic acid, pyridinium salt is separated by filtration.

$R_f$ = 0.34 (± 0.10) in the system methylisobutylketone/methanol/formic acid 60/6/2, detection with bromcresol green and KMnO$_4$; nmr : 1.00 t (3H) (J 6.6 c./sec.), 2.02 s (3H), 3.00 q (2H) (J 6.6 c./sec.), 3.28 d (1H) (J 17 c./sec.), 3.69 d (1H) (J 17 c./sec.), 5.05 d (1H) (J 5 c./sec.), 5.65 d (1H) (J 5 c./sec.), pyridinium : 7.55 m (2H), 7.90 m (1H), 8.65 m (2H).

EXAMPLE 6

In a one liter reaction flask and to a 6.888 g. aliquot of 7-amino-3-(2-methyl-1,3,4-thiadiazol-5-ylthiomethyl)-3-cephem-4-carboxylic acid prepared according to the procedure described in Example 1, are added pyridine (500 ml) and ethylisocyanate (2.4 ml). The mixture is heated to 50° C and stirred for 3 hrs at that temperature. The solvent is then removed by evaporation under reduced pressure and the residue is taken up in acetic acid (20 ml) and ethyl acetate (250 ml).

After filtration, ethyl ether is added to precipitate 7-(3-ethylureido)-3-(2-methyl-1,3,4-thiadiazol-5-ylthiomethyl)-3-cephem-4-carboxylic acid.

$R_f$ = 0.17 (± 0.10) in the system methylisobutylketone/methanol/formic acid 60/6/2, detection with bromcresol green and KMnO$_4$; nmr : 1.00 t (3H) (J 7.3 c./sec.), 2.70 s (3H), 3.00 q (2H) (J 7.3 c./sec.), 3.51 d (1H) (J 17 c./sec.), 3.88 d (1H) (J 17 c./sec.), 4.20 d (1H) (J 12 c./sec.), 4.58 d (1H) (J 12 c./sec.), 5.08 d (1H) (J 5.2 c./sec.), 5.68 d (1H) (J 5.2 c./sec.).

EXAMPLE 7

In a one liter reaction flask and to a 6.528 g aliquot of 7-amino-3-(2-thiazolin-2-ylthiomethyl)-3-cephem-4-carboxylic acid prepared according to the procedure described in Example 3 are added methylene chloride (500 ml), triethylamine (5.6 ml) and ethylisocyanate (2.4 ml). The mixture is stirred at room temperature for 17 hrs and then at 50° C for 1 hour. The solvent is then removed by evaporation under reduced pressure and the residue is taken up in acetic acid (20 ml) and ethylacetate (250 ml).

After filtration, ethyl ether is added to precipitate 7-(3-ethylureido)-3-(2-thiazolin-2-ylthiomethyl)-3-cephem-4-carboxylic acid.

$R_f$ = 0.17 (± 0.10) in the system methylisobutylketone/methanol/formic acid 60/6/2, detection with bromcresol green and KMnO$_4$; nmr : 1.18 t (3H) (J 7.0 c./sec.), 2.70–3.30 m (2H + 2H), 3.01 q (2H) (J 7.0 c./sec.), 3.30 d (1H) (J 16 c./sec.), 3.70 d (1H) (J 16 c./sec.), 4.10 d (1H) (J 8 c./sec.) 4.35 d (1H) (J 8 c./sec.), 4.98 d (1H) (J 5 c./sec.), 5.58 d (1H) (J 5 c./sec.).

EXAMPLE 8

In a one liter reaction flask and to a 6.888 g aliquot of 7-amino-3-(2-methyl-1,3,4-thiadiazol-5-ylthiomethyl)-3-cephem-4-carboxylic acid prepared according to the procedure of Example 1, is added methylene chloride (500 ml), triethylamine (5.6 ml) and 2-chloroethylisocyanate (4.2 ml). The mixture is stirred for 10 hrs at room temperature. The solvent is then removed by evaporation under reduced pressure at a temperature inferior to 40° C and the residue is taken up in acetic acid (20 ml) and ethyl acetate (250 ml).

After filtration, ethyl ether (2 l.) is added to precipitate 7-[3-(2-chloro-ethylureido)]-3-(2-methyl-1,3,4-thiadiazol-5-ylthiomethyl)-3-cephem-4-carboxylic acid (7.54 g), crystallizing with 1.5 mole of ether.

$R_f$ = 0.49 (± 0.10) in the system acetonitrile/methanol/water 6/3/1, U.V. detection; nmr : 2.67 s (3H), 2.8–3.4 m (2H + 2H), 3.39 d (1H) (J 16 c./sec.), 3.72 d (1H) (J 16 c./sec.), 4.21 d (1H) (J 13 c./sec.), 4.59 d (1H) (J 13 c./sec.), 5.01 d (1H) (J 5.3 c./sec.), 5.58 d (1H) (J 5.3 c./sec.).

Using the same procedure, the following cephalosporins are obtained:

7-[3-(2-chloro-ethylureido)]-3-(2-methyl-1,3,4-oxadiazol-5-ylthiomethyl)-3-cephem-4-carboxylic acid. nmr : 2.47 s (3H), 3.40–3.75 m (2H + 2H + 2H), 4.38 s (2H), 5.06 d (1H) (J 5 c./sec.), 5.75 d (1H) (J 5 c./sec.).

7-[3-(2-chloro-ethylureido)]-3-(2-methyl-1,3,4-triazol-5-ylthiomethyl)-3-cephem-4-carboxylic acid. nmr : 2.66 s (3H), 3.40–3.80 m (2H + 2H + 2H), 4.20–4.60 m (2H), 5.01 d (1H) (J 5 c./sec.), 5.7 d (1H) (J 5.3 c./sec.).

7-[3-(2-chloro-ethylureido)]-3-(pyrimidin-2-ylthiomethyl)-3-cephem-4-carboxylic acid. nmr : 3.51 d (1H) (J 18 c./sec.), 3.59 t (2H) (J 6.7 c./sec.), 3.65 t (2H) (J 6.7 c./sec.), 3.88 d (1H) (J 18 c./sec.), 4.08 d (1H) (J 13 c./sec.), 4.74 d (1H) (J 13 c./sec.), 5.11 d (1H) (J 5.1 c./sec.), 5.78 d (1H) (J 5.1 c./sec.), 7.29 t (1H) (J 5 c./sec.), 8.69 d (2H) (J 5.0 c./sec.).

7-[3-(2-chloro-ethylureido)]-3-(1,3,4-oxadiazol-2-ylthiomethyl)-3-cephem-4-carboxylic acid. nmr : 3.4∼3.8 m (2H + 2H + 2H), 4.4 m (2H), 5.0 d (1H) (J 5 c./sec.), 5.58 d (1H) (J 5 c./sec.), 9.52 s (1H).

7-[3-(2-chloro-ethylureido)]-3-(1,3,4-triazol-2-ylthiomethyl)-3-cephem-4-carboxylic acid nmr : 3.4–4.0 m (2H + 2H + 2H), 4.2–4.8 m (2H), 5.00 d (1H) (J 5 c./sec.), 5.55 d (1H) (J 5 c./sec.), 9.18 s (1H).

7-[3-(2-chloro-ethylureido)]-3-(1-methyl-1H-tetrazol-5-ylthiomethyl)-3-cephem-4-carboxylic acid. nmr : 3.3–3.4 m (2H + 2H), 3.60 m (2H), 3.93 s (3H), 4.3 m (2H), 4.95 d (1H) (J 5 c./sec.), 5.53 d (1H) (J 5 c./sec.).

EXAMPLE 9

In a one liter reaction flask and to a 6.888 g. aliquot of 7-amino-3-(2-methyl-1,3,4-thiadiazol-5-ylthiomethyl)-3-cephem-4-carboxylic acid prepared according to the procedure described in Example 1, is added n.propylisocyanate (2.9 ml) in pyridine (250 ml). The mixture is stirred for 4 hrs. at room temperature. The solvent is then removed by evaporation under reduced pressure and the residue is taken up in acetic acid (10 ml) and ethyl acetate (125 ml).

After filtration, ethyl ether is added to precipitate 7-(3-n.propylureido)-3-(2-methyl-1,3,4-thiadiazol-5-ylthiomethyl)-3-cephem-4-carboxylic acid.

$R_f$ = 0.39 (± 0.10) in the system acetonitrile/water 80/20, detection with bromcresol green and $KMnO_4$; nmr : 0.83 t (3H) (J 6.6 c./sec.), 1.35 m (2H) (J 6.6 c./sec.), 2.70 s (3H), 3.03 t (2H) (J 6.6 c./sec.), 3.55 d (1H) (J 17 c./sec.), 3.85 d (1H) (J 17 c./sec.), 4.20 d (1H) (J 13 c./sec.), 4.56 d (1H) (J 13 c./sec.), 5.11 d (1H) (J 5.3 c./sec.), 5.70 d (1H) (J 5.3 c./sec.).

Using the same procedure, the following cephalosporins are obtained:

7-(3-n.propylureido)-3-(2-methyl-1,3,4-oxadiazol-5ylthiomethyl)-3-cephem-4-carboxylic acid. nmr : 0.89 t (3H) (J 7.0 c./sec.), 1.4 m (2H) (J 7.0 c./sec.), 2.49 s (3H), 3.4 m (2H), 3.51 d (1H (J 18 c./sec.), 3.86 d (1H) (J 18 c./sec.), 4.38 s (2H), 5.12 d (1H) (J 5 c./sec.), 5.74 d (1H) (J 5 c./sec.).

7-(3-n.propylureido)-3-(pyrimidin-2-ylthiomethyl)-3-cephem-4-carboxylic acid. nmr : 0.86 t (3H) (J 7.5 c./sec.), 1.37 m (2H) (J 7.5 c.sec.), 3.06 t (2H) (J 7.5 c./sec.), 3.50 d (1H) (J 16.5 c./sec.), 3.89 d (1H) (J 16.5 c./sec.), 6.02 d (1H) (J 14 c./sec.), 6.70 d (1H) (J 14 c./sec.), 5.08 d (1H) (J 4.9 c./sec.), 5.73 d (1H) (J 4.9 c./sec.), 7.25 t (1H) (J 5 c./sec.), 8.57 d (2H) (J 5 c./sec.).

7-(3-n.propylureido)-3-(1,3,4-oxadiazol-2-ylthiomethyl)-3-cephem-4-carboxylic acid. nmr : 0.89 t (3H) (J 7.3 c./sec.), 1.4 m (2H) (J 7.3 c./sec.), 3.1 t (2H) (J 7.3 c./sec.), 3.48 d (1H) (J 17 c./sec.), 3.84 d (1H) (J 17 c./sec.), 4.29 d (1H) (J 13 c./sec.), 4.56 d (1H) (J 13 c./sec.), 5.09 d (1H) (J 5.3 c./sec.), 5.74 d (1H) (J 5.3 c./sec.).

7-(3-n.propylureido)-3-(1-methyl-1,3,4-triazol-2-ylthiomethyl)-3-cephem-4-carboxylic acid. nmr : 0.86 t (3H) (J 7 c./sec.), 1.3 m (2H), 3.25 m (2H), 3.60 m (2H), 3.97 s (3H), 4.32 m (2H), 5.00 d (1H) (J 5.2 c./sec.), 5.59 d (1H) (J 5.2 c./sec.).

EXAMPLE 10

In a one liter reaction flask and to 5.360 g. of 7-amino-3-desacetoxy-cephalosporanic acid (7ADCA) are added chloroform (250 ml), triethylamine (10 ml) and isopropylisocyanate 3.7 ml). The mixture is heated to 50° C for 10 hrs. The unreacted 7-ADCA is separated by filtration. The solvent is removed by evaporation under reduced pressure, the residue is dissolved in acetone and precipitated by addition of ethyl ether.

After filtration, the precipitate is taken up in acetic acid (30 ml) from which 7-(3-isopropylureido)-3-desacetoxy-cephalosporanic acid precipitates by addition of ethyl ether (200 ml).

$R_f$ = 0.25 (± 0.10) in the system methylisobutylketone/methanol/formic acid 60/6/2, detection with bromcresol green and $KMnO_4$; nmr : 1.04 d (6H) (J 6.6 c./sec.), 2.01 s (3H), 2.8–3.5 m (1H) (J 6.6 c./sec.), 3.29 d (1H) (J 15.5 c./sec.), 3.67 d (1H) (J 15.5 c./sec.), 5.02 d (1H) (J 4.8 c./sec.), 5.60 d (1H) (J 4.8 c./sec.).

EXAMPLE 11

In a one liter reaction flask and to a 6.888 g. aliquot of 7-amino-3-(2-methyl-1,3,4-thiadiazol-5-ylthiomethyl)-3-cephem-4-carboxylic acid prepared according to the procedure described in Example 1, is added isopropylisocyanate (3 ml) in pyridine (500 ml). The mixture is heated to 50° C and stirred for 6 hrs at that temperature. The solvent is then removed by evaporation under reduced pressure and the residue is taken up in acetic acid (20 ml) and ethyl acetate (250 ml).

After filtration, ethyl ether is added to precipitate 7-(3-isopropylureido)-3-(2-methyl-1,3,4-thiadiazol-5-ylthiomethyl)-3-cephem-4-carboxylic acid (5.78 g).

$R_f$ = 0.19 (± 0.10) in the system methylisobutylketone/methanol/formic acid 60/6/2, detection with bromcresol green and $KMnO_4$; nmr : 1.05 d (6H) (J 6.6 c./sec.), 2.69 s (3H), 2.8–3.5 m (1H) (J 6.6 c./sec.), 3.49 d (1H) (J 15 c./sec.), 3.85 d (1H) (J 15 c./sec.), 4.23 d (1H) (J 13 c./sec.), 4.59 d (1H) (J 13 c./sec.), 5.10 d (1H) (J 5.2 c./sec.), 5.71 d (1H) (J 5.2 c./sec.).

EXAMPLE 12

In a one liter reaction flask and to a 6.528 g. aliquot of 7-amino-3-(2-thiazolin-2-ylthiomethyl)-3-cephem-4-carboxylic acid prepared according to the procedure described in Example 3, are added methylene chloride (500 ml), triethylamine (5.6 ml) and isopropylisocyanate (3ml). The mixture is stirred at room temperature for 18 hrs. The solvent is then removed by evaporation under reduced pressure and the residue is taken up in acetic acid (20 ml) and ethyl acetate (250 ml).

After filtration, ethyl ether is added to the filtrate to precipitate 7-(3-isopropylureido)-3-(2-thiazolin-2-ylthiomethyl)-3-cephem-4-carboxylic acid.

$R_f$ = 0.24 (± 0.10) in the system methylisobutylketone/methanol/formic acid 60/6/2, detection with bromcresol green and $KMnO_4$; nmr : 1.05 d (6H) (J 6.6 c./sec.), 2.8–3.5 m (2H + 2H + 1H), 3.30 d (1H) (J 14 c./sec.), 3.65 d (1H) (J 14 c./sec.), 4.07 d (1H) (J 15 c./sec.), 4.40 d (1H) (J 15 c./sec.), 4.98 d (1H) (J 5.2 c/sec.), 5.57 d (1H) (J 5.2 c./sec.).

EXAMPLE 13

In a one liter reaction flask and to 5.360 g. of 7-amino-3-desacetoxy-cephalosporanic acid (7-ADCA) are added pyridine (500 ml) and allylisocyanate (3.3 ml). The mixture is heated to 50° C for 5 hrs. The solvent is removed by evaporation under reduced pressure, the residue is taken up in acetic acid (20 ml) and ethyl acetate (250 ml) from which 7-(3-allylureido)-3-desacetoxy-cephalosporanic acid (6.480 g) precipitates by addition of ethyl ether (100 ml).

$R_f$ = 0.28 (± 0.10) in the system methylisobutylketone/methanol/formic acid 60/6/2; detection with bromcresol green and $KMnO_4$; nmr : 2.00 s (3H), 3.26 d (1H) (J 17 c./sec.), 3.65 d (1H) (J 17 c./sec.), 3.5–3.9 m (2H), 5.02 d (1H) (J 4.6 c./sec.), 5.0–5.4 m (2H), 5.6 d (1H) (J 4.6 c./sec.), 5.6–5.9 m (1H).

EXAMPLE 14

In a one liter reaction flask and to a 6.528 g. aliquot of 7-amino-3-(2-thiazolin-2-yl)-3-cephem-4-carboxylic acid prepared according to the procedure described in Example 3 are added chloroform (500 ml), triethylamine (5.6 ml) and allylisocyanate (2.65 ml). The mixture is stirred at room temperature for 3 hrs. The solvent is removed by evaporation under reduced pressure and the residue is taken up in acetic acid (20 ml) and ethyl acetate (250 ml).

After filtration, ethyl ether is added to the filtrate to precipitate 7-(3-allylureido)-3-(2-thiazolin-2-ylthiomethyl)-3-cephem-4-carboxylic acid.

$R_f$ = 0.14 (± 0.10) in the system methylisobutylketone/methanol/formic acid 60/6/2, detection with bromcresol green and $KNnO_4$; nmr : 3.3–3.9 m (2H + 2H + 2H), 3.9–4.2 m (2H), 4.08 d (1H) (J 12 c./sec.), 4.40 d (1H) (J 12 c./sec.), 4.98 d (1H) (J 5 c./sec), 5.0–5.4 m (2H), 5.62 d (1H) (J 5 c./sec.), 5.7–6.0 m (1H).

EXAMPLE 15

In a one liter reaction flask and to a 6.888 g. aliquot of 7-amino-3-(2-methyl-1,3,4-thiadiazol-5-ylthiomethyl)-3-cephem-4-carboxylic acid prepared according to the procedure described in Example 1, is added allylisocyanate (2.65 ml) in methylene chloride (500 ml) and triethylamine (5.6 ml). The mixture is stirred for 18 hrs at room temperature. The solvent is then removed by evaporation under reduced pressure and the residue is taken up in acetic acid (20 ml) and ethyl acetate (250 ml).

After filtration, ethyl ether is added to precipitate 7-(3-allylureido)-3-(2-methyl-1,3,4-thiadiazol-5-ylthiomethyl)-3-cephem-4-carboxylic acid.

$R_f$ = 0.12 (± 0.10) in the system methylisobutylketone/methanol/formic acid 60/6/2, detection with bromcresol green and $KMnO_4$; nmr : 2.68 s (3H), 3.40–3.90 m (2H + 2H), 4.22 d (1H) (J 13 c./sec.), 4.60 d (1H) (J 13 c./sec.), 5.0–5.40 m (2H), 5.01 d (1H) (J 5 c./sec.), 5.68 d (1H) (J 5 c./sec.), 5.7–6.0 m (1H).

Using the same procedure, the following cephalosporins are obtained:

7-(3-allylureido)-3-(2-methyl-1,3,4-oxadiazol-5-ylthiomethyl)-3-cephem-4-carboxylic acid. nmr : 2.47 s (3H), 3.4–3.8 m (2H + 2H), 6.22 d (1H) (J 18.6 c./sec.), 6.52 d (1H) (J 18.6 c./sec.), 5.00 d (1H) (J 5.3 c./sec.), 5.0–5.2 m (2H), 5.7 d (1H) (J 5.3 c./sec.), 5.6–6.2 m (2H).

7-(3-allylureido)-3-(2-methyl-1,3,4-triazol-5-ylthiomethyl)-3-cephem-4-carboxylic acid. nmr : 2.62 s (3H), 3.3–4.05 m (2H + 2H + 2H), 5.01 d (1H) (J 5.3 c./sec.), 5.20 m (2H, 5.69 d (1H) (J 5.3 c./sec.), 5.8–6.3 m (1H)

7-(3-allylureido)-3-(pyrimidin-2-ylthiomethyl)-3-cephem-4-carboxylic acid. nmr : 3.50 d (1H) (J 18 c./sec.), 3.92 d (1H) (J 18 c./sec.), 4.07 d (1H) (J 14 c./sec.), 4.73 d (1H) (J 14 c./sec.), 4.9–5.3 m (2H), 5.12 d (1H) (J 5 c./sec.), 5.6–6.3 m (1H), 5.80 d (1H) (J 5 c./sec.), 7.3 t (1H) (J 5.2 c./sec.), 8.7 d (2H) (J 5.2 c./sec.).

7-(3-allylureido)-3-(1-methyl-1H-tetrazol-5-ylthiomethyl)-3-cephem-4-carboxylic acid. nmr : 3.66 m (2H), 3.96 s (3H), 4.35 m (2H), 5.0 d (1H) (J 5 c./sec.), 5.27 m (2H), 5.60 d (1H) (J 5 c./sec.), 5.60–6.2 m (1H).

7-(3-allylureido)-3-(1,3,4-oxadiazol-2-ylthiomethyl)-3-cephem-4-carboxylic acid. nmr: 3.70 m (2H), 4.4 m (2H), 4.99 d (1H) (J 5 c./sec.), 5.22 m (2H), 5.57 d (1H) (J 5 c./sec.), 5.60–6.10 m (1H), 9.5 s (1H).

7-(3-allylureido)-3-(1,3,4-triazol-2-ylthiomethyl)-3-cephem-4-carboxylic acid. nmr : 3.75 m (2H), 4.3 m (2H), 5.10 d (1H) (J 5 c./sec.) 5.32 m (2H), 5.72 d (1H) (J 5 c./sec.), 5.70–6.15 m (1H), 9.25 s (1H).

EXAMPLE 16

In a one liter reaction flask and to a 6.888 g. aliquot of 7-amino-3-(2-methyl-1,3,4-thiadiazol-5-ylthiomethyl)-3-cephem-4-carboxylic acid prepared according to the procedure described in Example 1, is added n.butylisocyanate (3.3 ml) in pyridine (500 ml). The mixture is heated to 70° C and stirred for one hour at that temperature. The solvent is then removed by evaporation under reduced pressure and the residue is taken up in acetic acid (20 ml) and ethyl acetate (250 ml).

After filtration, ethyl ether is added to the filtrate to precipitate 7-(3-n.butylureido)-3-(2-methyl-1,3,4-thiadiazol-5-ylthiomethyl)-3-cephem-4-carboxylic acid.

$R_f$ = 0.48 (± 0.10) in the system acetonitrile/water 80/20, detection with bromcresol green and $KMnO_4$; nmr : 0.88 t (3H) (J 6 c./sec.), 1.0–1.5 m (2H + 2H) (J 6 c./sec.), 2.67 s (3H), 3.02 m (2H) (J 6 c./sec.), 3.52 d (1H) (J 14 c./sec.), 3.83 d (1H) (J 14 c./sec.), 4.21 d (1H) (J 13 c./sec.), 4.61 d (1H) (J 13 c./sec.), 5.10 d (1H) (J 5.2 c./sec.), 5.65 d (1H) (J 5.2 c./sec.).

EXAMPLE 17

7-ACA (13.65 g) and 5-mercapto-2-methyl-1,3,4-triazole (8.15 g) are suspended in 500 ml. of phosphate buffer 0.2 M ($Na_2HPO_4/NaH_2PO_4$) pH 6.5. To the suspension are added with stirring 10.93 g. of $NaHCO_3$. The reaction medium is heated for 80 minutes with stirring on a 80° C water bath. The solution is then treated with charcoal, cooled (5°–10° C) and acidified to pH 4 with 2 N hydrochloric acid. The obtained suspension is diluted with 150 ml. of acetone and stirred for 30 minutes. The precipitate is filtered, washed with water, acetone and ethyl ether and dried under reduced pressure to yield 7-amino-3-(2-methyl-1,3,4-triazol-5-ylthiomethyl)-3-cephem-4-carboxylic acid.

EXAMPLE 18

In a one liter reaction flask and to a 6.528 g. aliquot of 7-amino-3-(2-methyl-1,3,4-triazol-5-ylthiomethyl)-3-cephem-4-carboxylic acid prepared according to the procedure described in Example 17, are added pyridine (500 ml) and n.butylisocyanate (4.4 ml). The mixture is stirred at room temperature for 3 hrs. The solvent is then removed by evaporation under reduced pressure at a temperature inferior to 40° C and the residue is taken up in acetic acid (20 ml) and methanol (250 ml).

After filtration on charcoal, ethyl ether is added to the filtrate to precipitate 7-(3-n.butylureido)-3-(2-methyl-1,3,4-triazol-5-ylthiomethyl)-3-cephem-4-carboxylic acid.

$R_f$ = 0.51 (± 0.10) in the system acetonitrile/methanol/water 6/3/1, U.V. detection; nmr: 0.89 t (3H) (J 6.5 c./sec.), 1.1–1.7 m (2H + 2H), 2.35 s (3H, 3.13 t (2H) (J 6 c./sec.), 3.28 d (1H) (J 18 c./sec.), 3.75 d (1H) (J 18 c./sec.), 3.85 d (1H) (J 14 c./sec.), 4.17 d (1H) (J 14 c./sec.), 5.03 d (1H) (J 5.2 c./sec.), 5.54 d (1H) (J 5.2 c./sec.).

EXAMPLE 19

In a one liter reaction flask and to a 6.888 g. aliquot of 7-amino-3-(2-methyl-1,3,4-thiadiazol-5-ylthiomethyl)-3-cephem-4-carboxylic acid prepared according to the procedure described in Example 1, are added pyridine (500 ml) and n.hexylisocyanate (5.1 ml). The mixture is stirred to 70° C for 1 hour. The solvent is then removed by evaporation under reduced pressure at a temperature inferior to 40° C and the residue is taken up in acetic acid (20 ml) and ethyl acetate (250 ml).

After filtration, ethyl ether (270 ml) is added to the filtrate and the solvent is removed by evaporation under reduced pressure. The residue is taken up in ethanol (250 ml) and the solution is filtered on charcoal and concentrated by evaporation. By addition of water, 7-(3-n.hexylureido)-3-(2-methyl-1,3,4-thiadiazol-5-ylthiomethyl)-3-cephem-4-carboxylic acid (5.85 g) is obtained.

$R_f$ = 0.58 (± 0.10) in the system acetonitrile/methanol/water 6/3/1, U.V. detection; nmr: 0.88 t (3H) (J 5.9 c./sec.), 1.28 m (4 × 2H), 2.68 s (3H), 2.98 t (2H) (J 6.0 c./sec.), 3.51 d (1H) (J 17 c./sec.), 3.87 d (1H) (J 17 c./sec.), 4.21 d (1H) (J 13 c./sec.), 4.61 d (1H) (J 13 c./sec.), 5.09 d (1H) (J 5.2 c./sec.), 5.70 d (1H) (J 5.2 c./sec.).

EXAMPLE 20

In a one liter reaction flask and to 6.888 g. aliquot of 7-amino-3-(2-methyl-1,3,4-thiadiazol-5-ylthiomethyl)-3-cephem-4-carboxylic acid prepared according to the procedure described in Example 1, are added pyridine (500 ml) and benzylisocyanate (4 ml). The mixture is stirred at room temperature for 1 hour. The solvent is then removed by evaporation under reduced pressure at temperature inferior to 40° C and the residue is taken up in acetic acid (20 ml) and ethyl acetate (250 ml).

After filtration, the solvent is evaporated under reduced pressure. The residue is taken up in methanol (100 ml) and by addition of ethyl ether (2 l.) 7-(3-benzylureido)-3-(2-methyl-1,3,4-thiadiazol-5-ylthiomethyl)-3-cephem-4-carboxylic acid is obtained.

$R_f$ = 0.56 (± 0.10) in the system acetonitrile/methanol/water 6/3/1, detection with bromcresol green and $KMnO_4$; nmr: 2.6 s (3H), 3.4 m (2H), 4.3 m (2 × 2H), 5.0 d (1H) (J 4.9 c./sec.), 5.68 d (1H) (J 4.9 c./sec.), 7.25 m (5H).

Using the same procedure, the following cephalosporins are obtained:

7-(3-benzylureido)-3-(2-methyl-1,3,4-oxadiazol-5-ylthiomethyl)-3-cephem-4-carboxylic acid. nmr: 2.45 s (3H), 3.60 d (1H) (J 16 c./sec.), 3.86 d (1H) (J 16 c./sec.), 4.27 m (2H + 2H), 5.10 d (1H) (J 5 c./sec.), 5.73 d (1H) (J 5 c./sec.), 7.31 s (5H).

7-(3-benzylureido)-3-(pyrimidin-2-ylthiomethyl)-3-cephem-4-carboxylic acid. nmr: 3.48 d (1H) (J 17.4 c./sec.), 3.88 d (1H) (J 17.4 c./sec.), 4.06 d (1H) (J 13 c./sec.), 4.32 s (2H), 4.72 d (1H) (J 13 c./sec.), 5.10 d (1H) (J 5.1 c./sec.), 5.76 d (1H) (J 5.1 c./sec.), 7.22 t (1H) (J 5 c./sec.), 7.32 s (5H), 8.67 d (2H) (J 5 c./sec.).

7-(3-p-acetoxybenzylureido)-3-(2-methyl-1,3,4-thiadiazol-5-ylthiomethyl)-3-cephem-4-carboxylic acid. nmr: 2.24 s (3H), 2.66 s (3H), 3.52 m (2H), 4.27 s (2H), 4.22 d (1H) (J 13 c./sec.), 4.58 d (1H) (J 13 c./sec.), 5.00 d (1H) (J 5 c./sec.), 5.59 d (1H) (J 5 c./sec.), 7.14 d (2H) (J 8.5 c./sec.), 7.40 d (2H) (J 8.5 c./sec.).

7-(3-p-hydroxybenzylureido)-3-(2-methyl-1,3,4-thiadiazol-5-ylthiomethyl)-3-cephem-4-carboxylic acid. nmr: 2.70 s (3H), 3.72 m (1H + 1H), 4.18 s (2H), 4.25 d (1H) (J 14 c./sec.), 4.62 d (1H) (J 14 c./sec.), 5.15 d (1H) (J 5 c./sec.), 5.76 d (1H) (J 5 c./sec.), 6.82 d (2H) (J 9 c./sec.), 7.20 d (2H) (J 9 c./sec.).

7-(3-α-methylbenzylureido)-3-(2-methyl-1,3,4-thiadiazol-5-ylthiomethyl)-3-cephem-4-carboxylic acid. nmr: 1.35 d (3H) (J 7 c./sec.), 2.68 s (3H), 3.55 d (1H) (J 17 c./sec.), 3.88 d (1H) (J 17 c./sec.), 4.27 d (1H) (J 13 c./sec.), 4.6 d (1H) (J 13 c./sec.), 4.8 m (1H), 5.1 (1H) (J 5 c./sec.), 5.7 d (1H) (J 5 c./sec.), 7.37 s (5H).

7-(3-benzylureido)-3-(1,3,4-oxadiazol-2-ylthiomethyl)-3-cephem-4-carboxylic acid. nmr: 3.45~3.60 m (2H), 4.2~4.6 m (2H + 2H), 5.00 d (1H) (J 5 c./sec.), 5.64 d (1H) (J 5 c./sec.), 7.31 s (5H), 9.6 s (1H)

7-(3-p-chlorobenzylureido)-3-(2-methyl-1,3,4-thiadiazol-5-ylthiomethyl)-3-cephem-4-carboxylic acid. nmr: 2.68 s (3H), 3.44 d (1H) (J 17 c./sec.), 3.63 d (1H) (J 17 c./sec.), 4.30 s (2H), 4.32 d (1H) (J 13 c./sec.), 4.60 d (1H) (J 13 c./sec.), 5.00 d (1H) (J 5 c./sec.), 5.62 d (1H) (J 5 c./sec.), 7.4 s (4H).

7-(3-α-methylbenzylureido)-3-(1,3,4-oxadiazol-2-ylthiomethyl)-3-cephem-4-carboxylic acid. nmr: 1.35 d (3H) (J 5.7 c./sec.), 3.53 m (2H), 4.1–4.5 m (2H), 4.6–4.8 (1H), 4.95 d (1H) (J 5 c./sec,), 5.52 d (1H) (J 5 c./sec.), 7.36 s (5H), 9.58 s (1H).

7-(3-p-chlorobenzylureido)-3-(1,3,4-oxadiazol-2-ylthiomethyl)-3-cephem-4-carboxylic acid. nmr: 3.56 m (2H), 4.29 m (2H), 4.50 m (2H), 4.98 d (1H) (J 5 c./sec.), 5.59 d (1H) (J 5 c./sec.), 7.36 s (4H), 9.5 s (1H).

7-(3-α-methylbenzylureido)-3-(1,3,4-triazol-2-ylthiomethyl)-3-cephem-4-carboxylic acid. nmr: 1.34 d (3H) (J 7 c./sec.), 3.55 m (2H), 4.2–4.8 m (2H + 1H), 4.97 d (1H) (J 5 c./sec.), 5.50 d (1H) (J 5 c./sec.), 7.36 s (5H), 9.07 s (1H).

7-(3-α-methylbenzylureido)-3-(2-methyl-1,3,4-oxadiazol-5-ylthiomethyl)-3-cephem-4-carboxylic acid. nmr: 1.36 d (3H) (J 7.3 c./sec.), 2.46 s (3H), 3.53 m (2H), 4.3 m (2H) 4.74 q (1H) (J 7.3 c./sec.), 4.98 dd (1H) (J 5 c./sec.).

7-(3-p-chlorobenzylureido)-3-(2-methyl-1,3,4-oxadiazol-5-ylthiomethyl)-3-cephem-4-carboxylic acid. nmr: 2.46 s (3H), 3.36 d (1H), (J 16.3 c./sec.), 3.73 d (1H) (J 16.3 c./sec.), 4.2–4.4 m (2H + 2H), 5.00 d (1H) (J 5 c./sec.), 5.58 d (1H) (J 5 c./sec.), 7.38 s (4H).

7-(3-benzylureido)-3-(1-methyl-1H)-tetrazol-5-ylthiomethyl)-3-cephem-4-carboxylic acid. nmr: 3.41 d (1H) (J 16 c./sec.), 3.68 d (1H) (J 16 c./sec.), 4.20–4.40 m (2H + 2H), 4.97 d (1H) (J 5.3 c./sec.), 5.59 d (1H) (J 5.3 c./sec.), 7.33 s (5H).

7-(3-α-methylbenzylureido)-3-(1-methyl-1H-tetrazol-5-ylthiomethyl)-3-cephem-4-carboxylic acid. nmr: 1.36 d (3H) (J 7 c./sec.), 3.56 m (2H), 3.93 s (3H), 4.33 m (2H), 4.8 m (1H) 4.95 d (1H) (J 5.3 c./sec.), 5.56 d (1H) (J 5.3 c./sec.), 7.34 s (5H).

7-(3-p-chlorobenzylureido)-3-(1-methyl-1H-tetrazol-5-ylthiomethyl)-3-cephem-4-carboxylic acid. nmr: 3.6 m (2H), 3.92 s (3H), 4.1–4.2 m (2H + 2H), 4.96 d (1H) (J 5.5 c./sec.), 5.58 d (1H) (J 5.5 c./sec.), 7.37 s (4H).

7-(3-p-acetoxybenzylureido)-3-(1-methyl-1H-tetrazol-5-ylthiomethyl)-3-cephem-4-carboxylic acid. nmr: 2.25 s (3H), 3.42 d (1H) (J 16 c./sec.), 3.74 d (1H) (J 16 c./sec.), 3.92 s (3H), 4.99 d (1H) (J 5 c./sec.), 5.62 d (1H) (J 5 c./sec.), 7.15 d (2H) (J 9.5 c./sec.), 7.37 d (2H) (J 9.5 c./sec.).

7-(L(−)-3-α-methylbenzylureido)-3-(2-methyl-1,3,4-thiadiazol-5-ylthiomethyl)-3-cephem-4-carboxylic acid. nmr: 1.36 d (3H) (J 7 c./sec.), 2.69 s (3H), 3.56 d (1H) (J 18 c./sec.), 3.88 d (1H) (J 18 c./sec.), 4.24 d (1H) (J 13 c./sec.), 4.60 d (1H) (J 13 c./sec.), 4.82 q (1H) (J 7 c./sec.), 5.10 d (1H) (J 5 c./sec.), 5.71 d (1H) (J 5 c./sec.), 7.38 s (5H).

7-(L-(−)-3-α-methylbenzylureido)-3-(2-methyl-1,3,4-oxadiazol-5-ylthiomethyl)-3-cephem-4-carboxylic acid. nmr: 1.36 d (3H) (J 7 c./sec.), 2.46 s (3H), 3.70 m (2H), 4.14 d (1H) (J 13 c./sec.), 4.45 d (1H), (J 13 c./sec.), 4.81 q (1H) (J 7 c./sec.), 5.08 d (1H) (J 5.2 c./sec.), 5.70 d (1H) (J 5.2 c./sec.), 7.36 s (5H).

7-(L(−)-3-α-methylbenzylureido)-3-(1-methyl-1H-tetrazol-5-ylthiomethyl)-3-cephem-4-carboxylic acid. nmr: 1.36 d (3H) (J 6.7 c./sec.), 3.72 s (2H), 4.96 s (3H), 4.22 d (1H) (J 13.4 c./sec.), 4.46 d (1H) (J 13.4 c./sec.), 4.88 q (1H) (J 6.7 c./sec.), 5.09 d (1H) (J 5 c./sec.), 5.70 d (1H) (J 5 c./sec.), 7.37 s (5H).

7-(3-p-methoxybenzylureido)-3-(2-methyl-1,3,4-thiadiazol-5-ylthiomethyl)-3-cephem-4-carboxylic acid. nmr: 2.68 s (3H), 3.75 m + s (2H + 3H), 4.19 s (2H), 4.18 d (1H) (J 13.3 c./sec.), 4.56 d (1H) (J 13.3 c./sec.), 5.09 d (1H) (J 5.0 c./sec.), 5.72 d (1H) (J 5.0 c./sec.), 6.94 d (2H) (J 9.3 c./sec.), 7.28 d (2H) (J 9.3 c./sec.).

7-(3-p-methoxybenzylureido)-3-(2-methyl-1,3,4-oxadiazol-5-ylthiomethyl)-3-cephem-4-carboxylic acid. nmr: 2.46 s (3H), 3.75 m (2H), 3.76 s (3H), 4.20 m (2H + 2H), 5.10 d (1H) (J 5 c./sec.), 5.74 d (1H) (J 5 c./sec.), 6.94 d (2H) (J 9 c./sec.), 7.26 d (2H) (J 9 c./sec.).

7-(3-p-methoxybenzylureido)-3-(1-methyl-1H-tetrazol-5-ylthiomethyl)-3-cephem-4-carboxylic acid. nmr: 3.74 s (3H), 3.96 s (3H), 4.20 s (2H), 4.20 d (1H) (J 15 c./sec.), 4.46 d (1H) (J 15 c./sec.), 5.10 d (1H) (J 5 c./sec.), 5.75 d (1H) (J 5 c./sec.), 6.95 d (2H) (J 9 c./sec.), 7.28 d (2H) (J 9 c./sec.).

7-[3-(2,4-dichlorobenzyl)ureido]-3-(2-methyl-1,3,4-thiadiazol-5-ylthiomethyl)-3-cephem-4-carboxylic acid. nmr: 2.68 s (3H), 3.41 d (1H) (J 15 c./sec.), 3.73 d (1H) (J 15 c./sec.), 4.36 s (2H), 4.27 d (1H) (J 13 c./sec.), 4.61 (1H) (J 13 c./sec.), 5.02 d (1H) (J 5.2 c./sec.), 5.62 d (1H) (J 5.2 c./sec.), 7.47 m (2H), 7.63 m (1H).

7-[3-(2,4-dichlorobenzyl)ureido]-3-(2-methyl-1,3,4-oxadiazol-5-ylthiomethyl)-3-cephem-4-carboxylic acid. nmr: 2.48 s (3H), 3.43 d (1H) (J 16 c./sec.), 3.67 d (1H) (J 16 c./sec.), 4.33 m (2H + 2H), 5.01 d (1H) (J 5.0 c./sec.), 5.61 d (1H) (J 5.0 c./sec.), 7.47 m (2H), 7.63 m (1H).

7-[3-(2,4-dichlorobenzyl)ureido]-3-(1-methyl-1H-tetrazol-5-yl-thiomethyl)-3-cephem-4-carboxylic acid. nmr: 3.47 d (1H) (J 16 c./sec.), 3.72 d (1H) (J 16 c./sec.), 3.96 s (3H), 4.35 m (2H+2H), 5.01 d (1H) (J 5.0 c./sec.), 5.50 d (1H) (J 5.0 c./sec.), 7.45 m (2H), 7.61 m (1H)

7-(3-o-chlorobenzylureido)-3-(2-methyl-1,3,4-thiadiazol-5-ylthiomethyl)-3-cephem-4-carboxylic acid. nmr: 2.69 s (3H), 3.70 m (2H), 4.25–4.70 m (2H + 2H), 5.12 d (1H) (J 5 c./sec.), 5.74 d (1H) (J 5 c./sec.), 7.43 s (4H).

7-(3-o-chlorobenzylureido)-3-(2-methyl-1,3,4-oxadiazol-5-ylthiomethyl)-3-cephem-4-carboxylic acid. nmr: 2.48 s (3H), 3.72 m (2H), 4.20–4.45 m (2H + 2H), 5.12 d (1H) (J 5 c./sec.), 5.73 d (1H), (J 5 c./sec.), 7.43 s (4H).

7-(3-o-chlorobenzylureido)-3-(1-methyl-1H-tetrazol-5-ylthiomethyl)-3-cephem-4-carboxylique. nmr: 3.72 m (2H), 3.94 s (3H), 4.32 s (2H + 2H), 5.07 d (1H) (J 5 c./sec.), 5.69 d (1H) (J 5 c./sec.), 7.37 s (4H).

7-(3-p-methylbenzylureido)-3-(2-methyl-1,3,4-thiadiazol-5-ylthiomethyl)-3-cephem-4-carboxylic acid. nmr: 2.28 s (3H), 2.68 s (3H), 3.63 d (1H) (J 18 c.sec.), 3.88 d (1H) (J 18c./sec.), 4.22 s (2H), 4.22 d (1H)(14 c/sec.), 4.58 d (1H) (J 14 c./sec.), 5.12 d (1H) (J 5.7 c./sec.), 5.74 d (1H) (J 5.7 c./sec.), 7.19 s (4H).

7-(3-p-methylbenzylureido)-3-(2-methyl-1,3,4-oxadiazol-5-ylthiomethyl)-3-cephem-4-carboxylic acid. nmr: 2.25 s (3H), 2.44 s (3H), 3.50 d (1H) (J 18 c./sec.), 3.84 d (1H) (J 18 c./sec.), 4.11 d (1H), (J 14 c./sec.), 4.21 s (2H), 4.41 d (1H) (J 14 c./sec.), 5.06 d (1H) (J 5.1 c./sec.), 5.69 d (1H) (J 5.1 c./sec.), 7.15 s (4H).

7-(3-p-methylbenzylureido)-3-(1-methyl-1H-tetrazol-5-ylthiomethyl)-3-cephem-4-carboxylic acid. nmr: 2.26 s (3H), 3.72 m (2H), 3.92 s (3H), 4.21 s (2H), 4.30 m (2H), 5.06 d (1H) (J 5 c./sec.), 5.68 d (1H) (J 5 c./sec.), 7.15 s (4H).

7-[3-(3,4-dichlorobenzyl)ureido]-3-(1-methyl-1H-tetrazol-5-ylthiomethyl)-3-cephem-4-carboxylic acid. nmr: 3.75 m (2H), 3.99 s (3H), 4.32 m (2H + 2H), 5.10 d (1H) (J 5 c./sec.), 5.71 d (1H) (J 5 c./sec.), 7.23–7.73 m (3 × 1H).

7-[3-(3,4-dichlorobenzyl)ureido]-3-(2-methyl-1,3,4-thiadiazol-5-ylthiomethyl)-3-cephem-4-carboxylic acid. nmr: 2.68 s (3H), 3.50 d (1H) (J 17.4 c./sec.), 3.88 d (1H) (J 17.4 c./sec.), 4.20 d (1H) (J 13 c./sec.), 4.28 s (2H), 4.55 d (1H) (J 13 c./sec.), 5.09 d (1H) (J 5.1 c./sec.), 5.68 d (1H) (J 5.1 c./sec.), 7.18–7.73 m (3 × 1H).

7-[3-(3,4-dichlorobenzyl)ureido]-3-(2-methyl-1,3,4-oxadiazol-5-ylthiomethyl)-3-cephem-4-carboxylic acid. nmr: 2.48 s (3H), 3.56 d (1H) (J 16 c./sec.), 3.88 d (1H) (J 16 c./sec.), 4.16 d (1H) (J 13.4 c./sec.), 4.38 s (2H), 4.47 d (1H) (J 13.4 c./sec.), 5.11 d (1H) (J 5 c./sec.), 5.70 d (1H) (J 5 c./sec.), 7.20–7.76 m (3 × 1H).

7-(3-p-fluorobenzylureido)-3-(2-methyl-1,3,4-thiadiazol-5-ylthiomethyl)-3-cephem-4-carboxylic acid. nmr: 2.68 s (3H), 3.55 d (1H) (J 18 c./sec.), 3.88 d (1H) (J 18 c./sec.), 4.23 d (1H) (J 12.4 c./sec.), 4.28 s (2H), 4.58 d (1H) (J 12.4 c./sec.), 5.12 d (1H) (J 5 c./sec.), 5.72 d (1H) (J 5 c./sec.), 6.98–7.50 m (4H).

7-(3-p-fluorobenzylureido)-3-(2-methyl-1,3,4-oxadiazol-5-ylthiomethyl)-3-cephem-4-carboxylic acid. nmr: 2.48 s (3H), 3.72 m (2H), 4.27 m + s (2H + 2H), 5.10 d (1H) (J 5.0 c./sec.), 5.72 d (1H) (J 5.0 c./sec.), 7.00–7.54 m (4H).

7-(3-p-fluorobenzylureido)-3-(1-methyl-1H-tetrazol-5-ylthiomethyl)-3-cephem-4-carboxylic acid. nmr: 3.75 m (2H), 3.97 s (3H), 4.29 m (2H + 2H), 5.10 d (1H) (J 5.1 c./sec.), 5.73 d (H) (J 5.1 c./sec.), 7.00–7.56 m (4H).

7-(3-p-nitrobenzylureido)-3-(2-methyl-1,3,4-thiadiazol-5-ylthiomethyl)-3-cephem-4-carboxylic acid. nmr: 2.69 s (3H), 3.53 d (1H) (J 18.7 c./sec.), 3.86 d (1H) (J 18.7 c./sec.), 4.21 d (1H) (J 13.4 c./sec.), 4.41 s (2H), 4.57 d (1H) (J 13.4 c./sec.), 5.10 d (1H) (J 5.0 c./sec.), 5.69 d (1H) (J 5.0 c./sec.), 7.58 d (2H) (J 9.0 c./sec.), 8.25 d (2H) (J 9.0 c./sec.).

7-(3-p-nitrobenzylureido)-3-(2-methyl-1,3,4-oxadiazol-5-ylthiomethyl)-3-cephem-4-carboxylic acid. nmr: 2.47 s (3H), 3.72 m (2H), 4.29 m (2H), 4.42 s (2H), 5.10 d (1H) (5.0 c./sec.), 5.70 d (1H) (J 5.0 c./sec.), 7.58 d (2H) (J 9.3 c./sec.), 8.24 d (2H) (J 9.3 c./sec.).

7-(3-p-nitrobenzylureido)-3-(1-methyl-1H-tetrazol-5-ylthiomethyl)-3-cephem-4-carboxylic acid. nmr: 3.75 m (2H), 3.97 s (3H), 4.34 m (2H), 4.42 m (2H), 5.11 d (1H) (J 5.0 c./sec.), 5.72 d (1H) (J 5.0 c./sec.), 7.59 d (2H) (J 9.0 c./sec.), 8.27 d (2H) (J 9.0 c./sec.).

7-(3-p-nitrobenzylureido)-3-(1,2,3-triazol-5-ylthiomethyl)-3-cephem-4-carboxylic acid. nmr: 3.69 m (2H), 4.00 m (2H), 4.41 m (2H), 5.10 d (1H) (J 5.0 c./sec.), 5.66 d (1H) (J 5.0 c./sec.), 7.57 d (2H) (J 9.2 c./sec.), 7.99 s (1H), 8.25 d (2H) (J 9.2 c./sec.).

EXAMPLE 21

In a one liter reaction flask and to a 6.888 g. aliquot of 7-amino-3-(2-methyl-1,3,4-thiadiazol-5-ylthiomethyl)-3-cephem-4-carboxylic acid prepared according to the procedure described in Example 1, is added m.tolylisocyanate (4 ml) in methylene chloride (500 ml) and triethylamine (5.6 ml). The mixture is stirred at room temperature for 3 hrs. The solvent is then removed by evaporation under reduced pressure and the residue is taken up in acetic acid (20 ml) and ethyl acetate (250 ml)

After filtration, ethyl ether is added to precipitate 7-(3-m.tolyureido)-3-(2-methyl-1,3,4-thiadiazol-5-ylthiomethyl)-3-cephem-4-carboxylic acid (6.626 g).

$R_f$ = 0.28 (± 0.10) in the system methylisobutylketone/methanol/formic acid 60/6/2, detection with bromcresol green and $KMnO_4$; nmr: 2.25 s (3H), 2.64 s (3H), 3.40 d (1H) (J 14.5 c./sec.), 3.72 d (1H) (J 14.5 c./sec), 4.23 d (1H) (J 13 c./sec.), 4.62 d (1H) (J 13 c./sec.), 5.07 d (1H) (J 5 c./sec.), 5.63 d (1H) (J 5 c./sec.), 7.28 m (4H).

EXAMPLE 22

In a one liter reaction flask and to a 6.888 g aliquot of 7-amino-3-(2-methyl-1,3,4-thiadiazol-5-ylthiomethyl)-3-cephem-4-carboxylic acid prepared according to the procedure described in Example 1, is added p-fluorophenylisocyanate (2.9 ml) in methylene chloride (500 ml) and triethylamine (5.6 ml). The mixture is stirred at room temperature for 1½ hr. The solvent is then removed by evaporation under reduced pressure and the residue is taken up in acetic acid (20 ml) and ethyl acetate (250 ml).

After filtration, ethyl ether is added to precipitate 7-(3-p-fluorophenylureido)-3-(2-methyl-1,3,4-thiadiazol-5-ylthiomethyl)-3-cephem-4-carboxylic acid.

$R_f$ = 0.29 (± 0.10) in the system methylisobutylketone/methanol/formic acid 60/6/2 detection with bromcresol green and $KMnO_4$; nmr: 2.68 s (3H), 3.41 d (1H) (J 12 c./sec.), 3.70 d (1H) (J 12 c./sec.), 4.29 d (1H), (J 13 c./sec.), 4.62 d (1H) (J 13 c./sec.), 5.08 d (1H) (J 5.3 c./sec.), 5.72 d (1H) (J 5.3 c./sec.), 6.8–7.6 m (4H).

EXAMPLE 23

In a 1 liter reaction flask and to 5.360 g of 7-amino-3-desacetoxy-cephalosporanic acid (7-ADCA) are added pyridene (500 ml) and cyclohexylisocyanate (4.8 ml). The mixture is heated at 50° C for 4 hrs. and at 70° C for 3 hrs. The solvent is removed by evaporation under reduced pressure, the residue is taken up in acetic acid (20 ml) and ethyl acetate (250 ml) from which 7-(3-cyclohexylureido)-3-desacetoxy-cephalosporanic acid precipitates by addition of ethyl ether (one liter).

$R_f$ = 0.37 (± 0.10) in the system methylisobutylketone/methanol/formic acid 60/6/2, detection with bromcresol green and $KMnO_4$; nmr : 1.0-1.8 m (6H), 1.4-2.1 m (4H), 2.04 s (3H), 3.31 d (1H) (J 14.7 c./sec.), 3.4–3.9 m (1H), 3.66 d (1H) (J 14.7 c./sec.), 5.04 d (1H) (J 5.3 c./sec.), 5.61 d (1H) (J 5.3 c./sec.).

EXAMPLE 24

In a one liter reaction flask and to a 6.888 g aliquot of 7-amino-3-(2-methyl-1,3,4-thiadiazol-5-ylthiomethyl)-3-cephem-4-carboxylic acid prepared according to the procedure described in Example 1, is added cyclohexylisocyanate (3.8 ml) in pyridine (500 ml). The mixture is heated to 70° C and stirred for one hour at that temperature. The solvent is then removed by evaporation under reduced pressure and the residue is taken up in acetic acid (20 ml) and ethyl acetate (250 ml).

After filtration, ethyl ether is added to precipitate 7-(3-cyclohexylureido)-3-(2-methyl-1,3,4-thiadiazol-5-ylthiomethyl)-3-cephem-4-carboxylic acid.

$R_f$ = 0.46 (± 0.10) in the system acetonitrile/water 80/20, detection with bromcresol green and $KMnO_4$; nmr : 0.8–1.6 m (GH), 1.2–2.0 m (4H), 2.73 s (3H), 3.0–3.7 m (1H), 3.5–4.0 m (2H), 4.23 d (1H) (J 14.7 c./sec.), 4.60 d (1H) (J 14.7 c./sec.), 5.11 d (1H) (J 5.0 c./sec.), 5.71d(1H) (J 5.0 c./sec.).

EXAMPLE 25

When an equivalent amount of 2-cyanoethylisocyanate, ethoxycarbonylmethylisocyanate, 3-butoxypropylisocyanate, 3-nitropropylisocyanate, 2-dimethylaminoethylisocyanate, p-nitrophenylisocyanate, p-acetamidophenylisocyanate, p-hydroxyphenylisocyanate, p-cyanophenylisocyanate, p-sulfamoylphenylisocyanate, p-mercaptophenylisocyanate, p-methoxyphenyl-isocyanate, β-cyclohexylethylisocyanate, 2-chlorocyclohexylisocyanate, 3-cyclohexenylisocyanate, 1,2-dibromoethylisocyanate, p-methylthiophenylisocyanate, p-dimethylaminophenylisocyanate, 9-ethyl-3-carbazolylisocyanate (prepared according to Werner Siefken Ann. 562, 75-136, 1949) is substituted for methylisocyanate in the procedure of Example 2, the following cephalosporins are obtained:

7-[3-(2-cyanoethyl)ureido]-3-[2-methyl-1,3,4-thiadiazol-5-ylthiomethyl]-3-cephem-4-carboxylic acid 7-[3-ethoxycarbonylmethyl ureido]-3-[2-methyl-1,3,4-thiadiazol-5-ylthiomethyl]-3-cephem-4-carboxylic acid 7-[3-(3-butoxypropyl)ureido]-3-[2-methyl-1,3,4-thiadiazol-5-ylthiomethyl]-3-cephem-4-carboxylic acid 7-[3-(3-nitropropyl)ureido]-3-[2-methyl-1,3,4-thiadiazol-5-ylthiomethyl]-3-cephem-4-carboxylic acid 7-[3-(2-dimethylaminoethyl)ureido]-3-[2-methyl-1,3,4-thiadiazol-5-ylthiomethyl]-3-cephem-4-carboxylic acid 7-[3-(p-nitrophenyl)ureido]-3-[2-methyl-1,3,4-thiadiazol-5-ylthiomethyl]-3-cephem-4-carboxylic acid 7-[3-(p-acetamidophenyl)ureido]-3-[2-methyl-1,3,4-thiadiazol-5-ylthiomethyl]-3-cephem-4-carboxylic acid 7-[3-(p-hydroxyphenyl)ureido]-3-[2-methyl-1,3,4-thiadiazol-5-ylthiomethyl]-3-cephem-4-carboxylic acid 7-[3-(p-cyanophenyl)ureido]-3-[2-methyl-1,3,4-thiadiazol-5-ylthiomethyl]-3-cephem-4-carboxylic acid 7-[3-(p-sulfamoylphenyl)ureido]-3-[2-methyl-1,3,4-thiadiazol-5-ylthiomethyl]-3-cephem-4-carboxylic acid 7-[3-(p-mercaptophenyl)ureido]-3-[2-methyl-1,3,4-thiadiazol-5-ylthiomethyl]-3-cephem-4-carboxylic acid 7-[3-(p-methoxyphenyl)ureido]-3-[2-methyl-1,3,4-thiadiazol-5-ylthiomethyl]-3-cephem-4-carboxylic acid 7-[3-($\beta$-cyclohexylethyl)ureido]-3-[2-methyl-1,3,4-thiadiazol-5-ylthiomethyl]-3-cephem-4-carboxylic acid 7-[3-(2-chlorocyclohexyl)ureido]-3-[2-methyl-1,3,4-thiadiazol-5-ylthiomethyl]-3-cephem-4-carboxylic acid 7-[3-(3-cyclohexenyl)ureido]-3-[2-methyl-1,3,4-thiadiazol-5-ylthiomethyl]-3-cephem-4-carboxylic acid 7-[3-(1,2-dibromoethyl)ureido]-3-[2-methyl-1,3,4-thiadiazol-5-ylthiomethyl]-3-cephem-4-carboxylic acid 7-[3-(p-methylthiophenyl)ureido]-3-[2-methyl-1,3,4-thiadiazol-5-ylthiomethyl]-3-cephem-4-carboxylic acid 7-[3-(p-dimethylaminophenyl)ureido]-3-[2-methyl-1,3,4-thiadiazol-5-ylthiomethyl]-3-cephem-4-carboxylic acid 7-[3-(9-ethyl-3-carbazolyl)ureido]-3-[2-methyl-1,3,4-thiadiazolyl-5-ylthiomethyl]-3-cephem-4-carboxylic acid

EXAMPLE 26

When an equivalent amount of 1,2,2,2-tetrachloroethylisocyanate (prepared according to Henri Ulrich et al., Angew. Chem. Int. Ed. Engl. 6(7), 636-7, 1967) is substituted for methylisocyanate in the procedure of Example 2, the following cephalosporin is obtained:
7-[3-(1,2,2,2-tetrachloroethyl)ureido]-3-[2-methyl-1,3,4-thiadiazol-5-ylthiomethyl]-3-cephem-4-carboxylic acid.

EXAMPLE 27

When an equivalent amount of propargylisocyanate (prepared according to Kikumasa Sato Nippon Kagaku Zasshi 77, 1411–13, 1956) is substituted for methylisocyanate in the procedure of Example 2, the following cephalosporin is obtained:
7-[3-propargylureido]-3-[2-methyl-1,3,4-thiadiazol-5-ylthio-methyl]-3-cephem-4-carboxylic acid.

EXAMPLE 28

When an equivalent amount of $\alpha$-chlorostyrylisocyanate (prepared according to Ohoka M. et al., J. Org. Chem. 36(23), 3542–46, 1971) is substituted for methylisocyanate in the procedure of Example 2, the following cephalosporin is obtained:
7-[3$\alpha$-chlorostyryl)ureido]-3-[2-methyl-1,3,4-thiadiazol-5-ylthiomethyl]-3-cephem-4-carboxylic acid.

EXAMPLE 29

When an equivalent amount of 5-nitro-2-furylisocyanate (prepared according to Saikachi Harno et al., Yakugaku Zasshi 88(9), 1189–96, 1968) is substituted for methylisocyanate in the procedure of Example 2, the following cephalosporin is obtained: 7-[3-(5-nitro-2-furyl)ureido]-3-[2-methyl-1,3,4-thiadiazol-5-ylthiomethyl]-3-cephem-4-carboxylic acid.

EXAMPLE 30

When an equivalent amount of $\alpha$-bromobenzylisocyanate, $\alpha$-methoxybenzylisocyanate, $\alpha$-hydroxybenzylisocyanate, $\alpha$-azidobenzylisocyanate, $\alpha$-carboxybenzylisocyanate, $\alpha$-aminobenzylisocyanate (prepared according to Melvin S. Newman, J. Amer. Chem. Soc. 57, 732–5, 1935) is substituted for methylisocyanate in the procedure of Example 2, the following cephalosporins were obtained:
7-[3-(3-($\alpha$-bromobenzyl)ureido]-3-[2-methyl-1,3,4-thiadiazol-5-ylthiomethyl]-3-cephem-4-carboxylic acid 7-[3-($\alpha$-methoxybenzyl)ureido]-3-[2-methyl-1,3,4-thiadiazol-5-ylthiomethyl]-3-cephem-4-carboxylic acid 7-[3-($\alpha$-hydroxybenzyl)ureido]-3-[2-methyl-1,3,4-thiadiazol-5-ylthiomethyl]-3-cephem-4-carboxylic acid 7-[3-($\alpha$-azidobenzyl)ureido]-3-[2-methyl-1,3,4-thiadiazol-5-ylthiomethyl]-3-cephem-4-carboxylic acid 7-[3-($\alpha$-carboxybenzyl)ureido]-3-[2-methyl-1,3,4-thiadiazol-5-ylthiomethyl]-3-cephem-4-carboxylic acid 7-[3-($\alpha$-aminobenzyl)ureido]-3-[2-methyl-1,3,4-thiadiazol-5-ylthiomethyl]-3-cephem-4-carboxylic acid

EXAMPLE 31

When an equivalent amount of hydroxymethylisocyanate (prepared according to F. W. Hoover et al., J. Org. Chem. 28(7), 1825–30, 1963) is substituted for methylisocyanate in the procedure of Example 2, the following cephalosporin is obtained:
7-[3-hydroxymethylureido]-3-[2-methyl-1,3,4-thiadiazol-5-ylthiomethyl]-3-cephem-4-carboxylic acid

EXAMPLE 32

When an equivalent amount of one of the heterocyclic thiols listed below is substituted for 5-mercapto-2-methyl-1,3,4-thiadiazole in the procedure of Example 1, the corresponding 7-amino-3-(heterocyclicthiomethyl)-3-cephem-4-carboxylic acid is obtained:

2-mercapto-5-methyl-1,3,4-oxadiazole
2-mercapto-1,3,4-oxadiazole
3-mercapto-5-methyl-1,2,4-thiadiazole
3-mercapto-1,2,4-thiadiazole
5-mercapto-1,2,4-thiadiazole
2-mercapto-1,3,4-thiadiazole
2-mercaptopyrimidine
2-mercapto-4-methylpyrimidine
2-mercapto-5-methylpyrimidine
2-mercapto-5-methoxypyrimidine
4-mercapto-5,6-dimethoxypyrimidine
3-mercaptopyridazine
3-mercapto-6-methylpyridazine
6-bromo-3-mercaptopyridazine
2-mercaptopyridine
4-mercaptopyridine
2-mercapto-6-methylpyridine
2-mercapto-5-nitropyridine
2-mercapto-4-methylthiazole

EXAMPLE 33

When an equivalent amount of the appropriate 7-amino-3-(heterocyclicthiomethyl)-3-cephem-4-carboxylic acid of Example 32 is substituted for 7-amino-3-(2-methyl-1,3,4-thiadiazol-5-ylthiomethyl)-3-cephem-4-carboxylic acid in the procedure of Example 1, the following cephalosporins are obtained:

7-(3-n.propylureido)-3-(5-methyl-1,2,4-thiadiazol-3-ylthiomethyl)-3-cephem-4-carboxylic acid
7-(3-n.propylureido)-3-(1,2,4-thiadiazol-3-ylthiomethyl)-3-cephem-4-carboxylic acid
7-(3-n.propylureido)-3-(1,2,4-thiadiazol-5-ylthiomethyl)-3-cephem-4-carboxylic acid
7-(3n.propylureido)-3-(1,3,4-thiadiazol-2-ylthiomethyl)-3-cephem-4-carboxylic acid
7-(3-n.propylureido)-3-(4-methylpryimidin-2-ylthiomethyl)-3-cephem-4-carboxylic acid
7-(3-n.propylureido)-3-(5-methylpyrimidin-2-ylthiomethyl)-3-cephem-4-carboxylic acid
7-(3-n.propylureido)-3-(5-methoxypyrimidin-2-ylthiomethyl)-3-cephem-4-carboxylic acid
7-(3-n.propylureido)-3-(5,6-dimethoxypyrimidin-4-ylthiomethyl)-3-cephem-4-carboxylic acid
7-(3-n.propylureido)-3-(pyridazin-3-ylthiomethyl)-3-cephem-4-carboxylic acid
7-(3-n.propylureido)-3-(6-methylpyridazin-3-ylthiomethyl)-3-cephem-4-carboxylic acid
7-(3-n,propylureido)-3-(6-bromopyridazin-3-ylthiomethyl)-3-cephem-4-carboxylic acid
7-(3-n.propylureido)-3-(pyrid-2-ylthiomethyl)-3-cephem-4-carboxylic acid
7-(3-n.propylureido)-3-(pyrid-4-ylthiomethyl)-3-cephem-4-carboxylic acid 7-(3-n.propylureido)-3-(6-methylpyrid-2-ylthiomethyl)-3-cephem-4-carboxylic acid
7-(3-n.propylureido)-3-(5-nitropyrid-2-ylthiomethyl)-3-cephem-4-carboxylic acid
7-(3-n.propylureido)-3-(4-methylpyrid-2-ylthiomethyl)-3-cephem-4-carboxylic acid

EXAMPLE 34

When an equivalent amount of one of the heterocyclic thiols listed below is substituted for 5-mercapto-2-methyl-1,3,4-thiadiazole in the procedure of Example 1, the corresponding 7-amino-3-(heterocyclicthiomethyl)-3-cephem-4-carboxylic acid is obtained:

2-mercapto-s-triazine
2-mercapto-4-methyl-s-triazine
3-mercapto-as-triazine
5,6-dimethyl-3-mercapto-as-triazine
1,5-dimethyl-3-mercaptopyrazole
2-mercapto-3-methoxypyrazine
5-mercapto-1-methyl-1,2,3-triazole
2-mercapto-5-methyl-1,3,4-triazole
3-mercapto-1-methyl-1,2,4-triazole
1-propyl-1H-tetrazole-5-thiol
3-mercapto-1-methyl-1,2,4-triazole
3-mercapto-5-methyl-1,2,4-triazole
3-mercapto-1,5-dimethyl-1,2,4-triazole
2-mercapto-1,3,4-triazole
5-mercapto-1,2,3-triazole
3-mercapto-1,2,4-triazole
5-mercaptotetrazole
2-mercaptopyrazine

EXAMPLE 35

When an equivalent amount of the appropriate 7-amino-3-(heterocyclicthiomethyl)-3-cephem-4-carboxylic acid of Example 34 is substituted for 7-amino-3-(2-methyl-1,3,4-thiadiazol-5-ylthiomethyl)-3-cephem-4-carboxylic acid in the procedure of Example 20, the following cephalosporins are obtained:

7-(3-benzylureido)-3-(s-triazin-2-ylthiomethyl)-3-cephem-4-carboxylic acid
7-(3-benzylureido)-3-(4-methyl-s-triazin-2-ylthiomethyl)-3-cephem-4-carboxylic acid
7-(3-benzylureido)-3-(as-triazin-3-ylthiomethyl)-3-cephem-4-carboxylic acid
7-(3-benzylureido)-3-(5,6-dimethyl-as-triazin-3-ylthiomethyl)-3-cephem-4-carboxylic acid
7-(3-benzylureido)-3-(1,5-dimethylpyrazol-3-ylthiomethyl)-3-cephem-4-carboxylic acid
7-(3-benzylureido)-3-(3-methoxypyrazin-2-ylthiomethyl)-3-cephem-4-carboxylic acid
7-(3-benzylureido)-3-(1-methyl-1,2,3-triazol-5-ylthiomethyl)-3-cephem-4-carboxylic acid
7-(3-benzylureido)-3-(5-methyl-1,3,4-triazol-2-ylthiomethyl)-3-cephem-4-carboxylic acid
7-(3-benzylureido)-3-(1-methyl-1,2,4-triazol-3-ylthiomethyl)-3-cephem-4-carboxylic acid
7-(3-benzylureido)-3-(1-propyl-1H-tetrazol-5-ylthiomethyl)-3-cephem-4-carboxylic acid
7-(3-benzylureido)-3-(1-methyl-1,2,4-triazol-3-ylthiomethyl)-3-cephem-4-carboxylic acid
7-(3-benzylureido)-3-(5-methyl-1,2,4-triazol-3-ylthiomethyl)-3-cephem-4-carboxylic acid
7-(3-benzylureido)-3-(1,5-dimethyl-1,2,4-triazol-3-ylthiomethyl)-3-cephem-4-carboxylic acid
7-(3-benzylureido)-3-(1,3,4-triazol-2-ylthiomethyl)-3-cephem-4-carboxylic acid
7-(3-benzylureido)-3-(1,2,3-triazol-5-ylthiomethyl)-3-cephem-4-carboxylic acid
7-(3-benzylureido)-3-(1,2,4-triazol-3-ylthiomethyl)-3-cephem-4-carboxylic acid
7-(3-benzylureido)-3-(tetrazol-5-ylthiomethyl)-3-cephem-4-carboxylic acid 7-(3-benzylureido)-3-(pyrazin-2-ylthiomethyl)-3-cephem-4-carboxylic acid

EXAMPLE 36

To a 6.888 g aliquot of 7-amino-3-(2-methyl-1,3,4-thiadiazol-5-ylthiomethyl)-3-cephem-4-carboxylic acid in a one liter reaction flask are added pyridene (500 ml), triethylamine (5.6 ml) and ethylisothiocyanate (3.5 ml). The mixture is heated with stirring at 50° C for 3 hrs. The solvent is then removed by evaporation under reduced pressure and the residue is taken up in acetic acid (20 ml) and ethyl acetate (250 ml).

After filtration, ethyl ether is added to precipitate 7-(3-ethylthiouredio)-3-(2-methyl-1,3,4-thiadiazol-5-ylthiomethyl)-3-cephem-4-carboxylic acid.

$R_f$ = 0.56 (± 0.10) in the system acetonitrile/methanol/water 6/3/1, U.V. detection.

EXAMPLE 37

To a cold solution (0° C) of 7-amino-3-(2-methyl-1,3,4-thiadiazol-5-ylthiomethyl)-3-cephem-4-carboxylic acid (6.888 g) in 80 ml. of methylene chloride is added trichlorsilane. The medium is stirred for 15 minutes at 20° C and 100 ml. of toluene is added. The solution is cooled up to −60° C and triethylamine (28 ml) and liquid (−70° C) phosgene (3.2 ml) are added. The medium is stirred for 3 hrs at −50° C. Most of the solvents is then eliminated under reduced pressure (1 mm Hg), the residual solution is allowed to reach room temperature and then immediately added to allylamine (0.888 ml) in methylene chloride (20 ml) with stirring for 10 hrs. After hydrolysis of the trimethylsilylester with water, the solvent is removed by evaporation and the residue is purified by chromatography on Silicagel Merck 0.2-0.06 mm to yield 7-(3-allylureido)-3-(2-methyl-1,3,4-thiadiazol-5-ylthiomethyl)-3-cephem-4-carboxylic acid with the same characteristics as the product obtained in Example 15.

EXAMPLE 38

A mixture of 7-ACA (6.8 g), pyridine (500 ml) and allylisocyanate (3.3 ml) is heated to 50° C for 1 hour. The solvent is removed by evaporation under reduced pressure and the residue is taken up with acetic acid (20 ml) and ethylacetate (250 ml). By addition of ether, 7-(3-allylureido)-cephalosporanic acid is obtained. ($R_f$ = 0.25 (± 0.10) in the system methylisobutylketone/methanol/formic acid 60/6/2, detection with bromcresol green and $KMnO_4$).

To a cool mixture of water (15 ml) and acetone (15 ml) is added a 5.31 g aliquot of the above obtained compound and, by small fractions, 26.7 ml of N NaHCO$_3$ and, thereafter, a mixture of 4.8 ml of 0.2 M NaH$_2$PO$_4$ and 25.2 ml of 0.2 M Na$_2$HOP$_4$. To the obtained solution, there is added a solution of 3.18 g of 5-mercapto-2-methyl-1,3,4-thiadiazole in 12 ml. of acetone and 18 ml. of N NaHCO$_3$.

The mixture is heated with stirring up to 70° C for 3 hrs. The solution is cooled, filtered on charcoal and acidified to pH 1 with 12 N HCl. The solution is clarified by addition of acetone, filtered on charcoal and the acetone is eliminated by evaporation under reduced pressure. The gummy residue is separated from the supernatent and taken up in a minimum methanol. The obtained precipitate is filtered to yield 7-(3-allylureido)-3-(2 - methyl - 1, 3, 4 - thiadiazol - 5 - ylthiomethyl) - 3 - cephem- 4 - carboxylic acid with the same characteristics as the product obtained in Example 15.

EXAMPLE 39

To a suspension of 7-ACA (5.45 g) in methylene chloride (50 ml) at 0° C under dried nitrogen, there is added at 0° C triethylamine (7 ml) and trimethylchlorsilane (6.4 ml) and the medium is allowed to react at that temperature for 15 minutes and then brought to room temperature. Toluene (40 ml) is added and the solution is cooled up to −70° C. Triethylamine (2.8 ml) and liquid phosgene (3.2 ml) at −70° C are added. The medium is allowed to react at −50° C for 3 hrs with stirring.

After filtration, most of the solvent is evaporated under reduced pressure (1 mm Hg) and the residual solution of trimethylsilyl-7-(isocyanato)-cephalosporanate is allowed to reach room temperature.

An aliquot of this solution containing 3.7 g. of trimethylsilyl-7-(isocyanato)-cephalosporanate is added to a solution of 0.9 ml. of allylamine in 50 ml. of methylenechloride. After a 10 hrs reaction period, the trimethylsilyl ester is hydrolized with water, the solvents are evaporated and the residue is purified by chromatography on Silicagel (Merck 0.06-0.2 mm), 7-(3-allylureido)-3-(2-methyl-1,3,4-thiadiazol-5-ylthiomethyl)-3-cephem-4-carboxylic acid with the same characteristics as the product obtained in Example 15 is obtained.

EXAMPLE 40

To a solution of 2-thenylamine (2.26 g) in methylenechloride is added slowly trimethylsilyl-7-(isocyanato)-cephalosporanate (3.7 g) obtained as indicated in the first paragraph of Example 39. The medium is stirred for one hour, the ester is then hydrolized with water. The solvents are eliminated under reduced pressure and the residue is purified by chromatography on Silicagel (Merek 0.06-0.2 mm) to obtain 7-[3-(2-thenyl)-ureido]-cephalosporanic acid.

To a solution of 7-[3-(2-thenyl)-ureido]-cephalosporanic acid (1.64 g) in 15 ml. of a ½ acetone/water mixture and 10 ml. of 0.6 N NaHCO$_3$, there is added 2-mercapto-5-methyl-1,3,4-thiadiazole (0.8 g) in acetone (20 ml). After a 4 hr reaction period at 65°–70° C, the solution is cooled and acidified to pH 3.7 with 12 N HCl. The obtained precipitate is filtered and dried to yield 7-[3-(2-thenyl)-ureido]-3-(2-methyl-1,3,4-thiadiazol-5-ylthiomethyl)-3-cephem-4-carboxylic acid.

nmr : 2.68 s (3H), 3.39 d (1H) (J 16 c./sec.), 3.71 d (1H) (J 16 c./sec.), 4.28 d (1H) (J 14 c./sec.), 4.60 d (1H) (J 14 c./sec.), 4.48 s (2H), 5.01 d (1H) (J 4.5 c./sec.), 5.63 d (1H) (J 4.5 c./sec.), 7.05 d (2H) (J 3 c./sec.), 7.46 t (1H) (J 3 c./sec.).

Using the same procedure, the following cephalosporins are obtained:
7-[3-(2-thenyl)-ureido]-3-(1-methyl-1H-tetrazol-5-ylthiomethyl)-3-cephem-4-carboxylic acid. nmr: 3.44 d (1H) (J 11 c./sec.), 3.70 d (1H) (J 11 c./sec.), 3.94 s (3H), 4.39 m (2H + 2H), 4.99 d (1H) (J 5 c./sec.), 5.60 d (1H) (J 5 c./sec.), 7.03 (2H) (J 3.3 c./sec.), 7.44 t (1H) (J 3.3 c./sec.). 7-(3-furfurylureido)-3-(2-methyl-1,3,4-thiadiazol-5-ylthiomethyl)-3-cephem-4-carboxylic acid. mmr: 2.69 s (3H), 3.53 d (1H) (J 18.6 c./sec.), 3.88 d (1H) (J 18.6 c./sec.), 4.20 d (1H) (J 13 c./sec.), 4.28 s (2H), 4.59 d (1H) (J 13 c./sec.), 5.13 d (1H) (J 5 c./sec.), 5.75 d (1H) (J 5 c./sec.), 6.28 d (1H) (J 3.4 c./sec.), 6.34 dd (1H) (J 3.4 c./sec. and 1.3 c./sec.), 7.64 d (1H) (J 1.3 c./sec.).

EXAMPLE 41

In a one liter reaction flask and to a 6.888 g. aliquot of 7-amino-3-(2-methyl-1,3,4-thiadiazol-5-ylthiomethyl)-3-cephem-4-carboxylic acid prepared according to the procedure described in Example 1, are added pyridine (500 ml) and phenethylisocyanate (5.9 ml). The mixture is stirred for 2 hrs. at room temperature. The solvent is then removed by evaporation under reduced pressure at a temperature inferior to 40° C and the residue is taken up in acetic acid (20 ml) and ethyl acetate (250 ml).

After filtration, the solvent is removed by evaporation under reduced pressure. The residue is taken up in methanol (100 ml) and by addition of ethyl ether (2.1.) 7-(3-phenethylureido)-3-(2-methyl-1,3,4-thiadiazol-5-ylthiomethyl)-3-cephem-4-carboxylic acid is obtained. nmr: 2.5–2.8 m + s (2H + 3H), 3.2–3.5 m (2H), 4.1–4.4 m (2H), 5.20–5.35 (1H), 5.59 d (1H) (J 4.0 c./sec.), 7.13 s (5H).

Using the same procedure, the following cephalosporinus are obtained: 7-(3-phenethylureido)-3-(2-methyl-1,3,4-triazol-5-ylthiomethyl)-3-cephem-4-carboxylic acid. nmr: 2.66 s (3H), 2.8 m (2H), 3.3 m (2H), 3.39 d (1H) (J 17 c./sec.), 3.80 d (1H) (J 17 c./sec.), 4.5 m (2H), 5.03 d (1H) (J 5.0 c./sec.), 5.68 d (1H) (J 5.0 c./sec.), 7.28 s (5H). 7-(3-phenethylureido)-3-(pyrimidin-2-ylthiomethyl)-3-cephem-4-carboxylic acid. nmr: 2.78 t (2H) (J 7.9 c./sec.), 3.15–3.45 m (2H), 3.37 d (1H) (J 16.7 c./sec.), 3.77 d (1H) (J 16.7 c./sec.), 4.25 d (1H) (J 14 c./sec.), 4.67 d (1H) (J 14 c./sec.), 5.05 d (1H) (J 5.2 c./sec.), 5.72 d (1H) (J 5.2 c./sec.), 7.17 t (1H) (J 5.0 c./sec.), 7.27 s (5H), 8.67 d (2H) (J 5.0 c./sec.). 7-(3-p-chlorophenethylureido)-3-(2-methyl-1,3,4-thiadiazol-5-ylthiomethyl)-3-cephem-4-carboxylic acid. nmr: 2.69 s (3H), 2.70 m (2H) (J 6.35 c./sec.), 3.20 t (2H) (J 6.35 c./sec.), 3.72 m (2H), 4.22 d (1H) (J 13.3 c./sec.), 4.57 d (1H) (J 13.3 c./sec.), 5.10 d (1H) (J 5 c./sec.), 5.70 d (1H) (J 5 c./sec.), 7.36 s (4H).

7-(3-p-chlorophenethylureido)-3-(2-methyl-1,3,4-oxadiazol-5-ylthiomethyl)-3-cephem-4-carboxylic acid nmr: 2.48 s (3H), 2.75 m (2H), 3.30 m (2H), 3.70 m (2H) 4.15 d (1H) (J 13.3 c./sec.), 4.48 d (1H) (J 13.3 c./sec.), 5.09 d (1H) (J 5 c./sec.), 5.72 d (1H) (J 5 c./sec.), 7.35 s (4H). 7-(3-p-chlorophenethylureido)-3-(1-methyl-1H-tetrazol-5-ylthio-methyl)-3-cephem-4-carboxylic acid. nmr: 2.70 t (2H) (J 6.5 c./sec.), 3.30 t (2H) (J 6.5 c./sec.), 3.72 m (2H), 3.95 s (3H), 4.20 d (1H) (J 13 c./sec.), 4.42 d (1H) (J 13 c./sec.), 5.08 d (1H) (J 5 c./sec.), 5.69 d (1H) (J 5 c./sec.), 7.32 s (4H).

We claim:
1. A compound of the formula

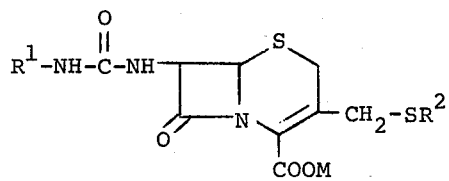

wherein
R¹ is thenyl or furfuryl;
R² is 1,3,4-thiadiazol-2-yl, 1,2,4-oxadiazol-3(5)-yl, 1,3,4-oxadiazol-2-yl, 1,2,3-triazol-5-yl, 1,2,4-triazol-3-yl, 1,3,4-triazol-2-yl, or tetrazol-5-yl, each of which may be unsubstituted or substituted with a lower alkyl group of 1 to 4 carbon atoms; and
M is hydrogen or an alkali metal cation.

2. A compound according to claim 1, being 7-[3-(2-thenyl)ureido]-3-(2methyl-1,3,4-thiadiazol-5-ylthiomethyl)-3-cephem-4-carboxylic acid.

3. A compound according to claim 1, being 7-[3-(2-thenyl)ureido]-3-(1-methyl-1H-tetrazol-5-ylthiomethyl)-3-cephem-4-carboxylic acid.

4. A compound according to claim 1, being 7-(3-furfurylureido)-3-(2-methyl-1,3,4-thiadiazol-5-ylthiomethyl)-3-cephem-4-carboxylic acid.

* * * * *